US012679847B1

(12) United States Patent
Haghdoost et al.

(10) Patent No.: US 12,679,847 B1
(45) Date of Patent: Jul. 14, 2026

(54) ARYL-SUBSTITUTED N-ALKYL INDOLES AND THEIR USE AS PHARMACOLOGICALLY ACTIVE AGENTS

(71) Applicant: Nalu Bio, Inc., San Francisco, CA (US)

(72) Inventors: Mehdi Haghdoost, Stittsville (CA); Caitlyn Krebs, San Francisco, CA (US); Grazia Piizzi, Brookline, MA (US); Phyllis Whiteley, Los Gatos, CA (US)

(73) Assignee: Nalu Bio, Inc., San Francisco, CA (US)

( * ) Notice: Subject to any disclaimer, the term of this patent is extended or adjusted under 35 U.S.C. 154(b) by 0 days.

(21) Appl. No.: 19/290,023

(22) Filed: Aug. 4, 2025

(51) Int. Cl.

| | |
|---|---|
| ***C07D 498/08*** | (2006.01) |
| ***A61K 9/00*** | (2006.01) |
| ***A61K 31/4725*** | (2006.01) |
| ***A61K 31/5377*** | (2006.01) |
| ***A61K 31/5386*** | (2006.01) |
| ***A61K 45/06*** | (2006.01) |
| ***A61K 47/10*** | (2017.01) |
| ***A61K 47/12*** | (2006.01) |
| ***A61K 47/26*** | (2006.01) |
| ***A61K 47/36*** | (2006.01) |
| ***A61K 47/44*** | (2017.01) |
| ***A61K 47/46*** | (2006.01) |
| ***A61P 15/00*** | (2006.01) |
| ***A61P 29/00*** | (2006.01) |
| ***C07D 401/06*** | (2006.01) |
| ***C07D 413/14*** | (2006.01) |

(52) U.S. Cl.

CPC .......... *C07D 498/08* (2013.01); *A61K 9/0036* (2013.01); *A61K 9/0056* (2013.01); *A61K 31/4725* (2013.01); *A61K 31/5377* (2013.01); *A61K 31/5386* (2013.01); *A61K 45/06* (2013.01); *A61K 47/10* (2013.01); *A61K 47/12* (2013.01); *A61K 47/26* (2013.01); *A61K 47/36* (2013.01); *A61K 47/44* (2013.01); *A61K 47/46* (2013.01); *A61P 15/00* (2018.01); *A61P 29/00* (2018.01); *C07D 401/06* (2013.01); *C07D 413/14* (2013.01)

(58) Field of Classification Search

CPC .. C07D 209/04; C07D 401/06; C07D 413/14; C07D 498/08; A61K 31/5377; A61K 31/5386; A61K 31/5725

See application file for complete search history.

(56) References Cited

U.S. PATENT DOCUMENTS

| | | | | |
|---|---|---|---|---|
| 2007/0213326 A1 | 9/2007 | Vidal | | |
| 2009/0143474 A1 * | 6/2009 | Royal | A61P 29/00 514/629 | |
| 2025/0101038 A1 | 3/2025 | Banister | | |

FOREIGN PATENT DOCUMENTS

| | | |
|---|---|---|
| WO | WO2024008341 A1 | 1/2024 |
| WO | WO2024178504 A1 | 9/2024 |

OTHER PUBLICATIONS

Grunewald (EMBO Molecular Medicine vol. 12 pp. 1-33 published 2020) (Year: 2020).*

Rieth (Cancers vol. 17 pp. 1-10 published online Apr. 1, 2025) (Year: 2025).*

* cited by examiner

*Primary Examiner* — George W Kosturko

(74) *Attorney, Agent, or Firm* — Dianne E. Reed; VLP Law Group LLP

(57) ABSTRACT

Disclosed herein are novel aryl-substituted N-alkyl indoles useful as pharmacologically active agents, the novel compounds having the structure of formula (I)

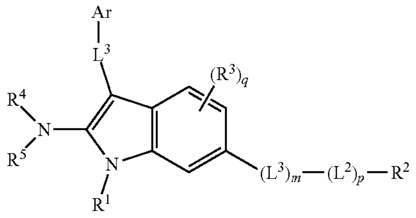

wherein m, p, q, $L^1$ through $L^3$, $R^1$ through $R^5$, and Ar are defined herein. Also provided are pharmaceutical formulations comprising at least one aryl-substituted N-alkyl indole of the invention, at least one pharmaceutically acceptable excipient, and, optionally, an additional beneficial agent, along with methods for treating a subject affected by a condition, disorder, or disease responsive to administration of the aryl-substituted N-alkyl indole. Exemplary methods of use include treatment of pain, treatment of inflammation, treatment of endometriosis, and a method for inducing weight loss.

24 Claims, 2 Drawing Sheets

ARYL-SUBSTITUTED N-ALKYL INDOLES AND THEIR USE AS PHARMACOLOGICALLY ACTIVE AGENTS

TECHNICAL FIELD

The present invention relates generally to novel pharmacologically active agents, and more particularly relates to substituted indoles having novel molecular structures. The invention has utility in the fields of medicine, medicinal chemistry, and therapeutics.

BACKGROUND

The potential medicinal properties of cannabinoids are attributed to specific interaction with the $CB_1$ and $CB_2$ receptors as well as many other receptors of the endocannabinoid system. These receptors are located in the brain and throughout the central and peripheral nervous systems. Activation of the $CB_1$ receptors, in particular, leads to inhibition of adenylyl cyclase activity and blockade of voltage-operated calcium channels, thereby suppressing neuronal excitability and serotonin neurotransmission inhibition. As a result, it has been suggested that cannabinoids that activate $CB_1$ receptors have potential utility in treatment of depression, neurological diseases, chronic pain, multiple sclerosis, glaucoma, and other conditions. See, e.g., Abioye et al. (2020), "$\Delta^9$-tetrahydrocannabivarin: a commentary on potential therapeutic benefit for the management of obesity and diabetes," *J. Cannabis Res.* 2:1-6.

$\Delta^9$-THC and other phytocannabinoids are, however, somewhat intoxicating, in turn rendering many of these compounds generally unsuitable as mainstream pharmaceutical agents. The intoxicating effects are believed to result from the fact that $\Delta^9$-THC and other intoxicating cannabinoids are partial agonists at both the $CB_1$ and $CB_2$ receptors (with somewhat greater affinity at the $CB_1$ receptor and greater selectivity at $CB_2$ receptors; see Rhee et al. (1997) *J. Med. Chem.* 40(20): 3228-33). There is, accordingly, a need for compounds, particularly non-cannabinoids, that provide the beneficial properties associated with intoxicating cannabinoids without the side effects typically seen with $\Delta^9$-THC. Ideally such non-cannabinoids exhibit moderate agonistic activity at the $CB_1$ and $CB_2$ receptors without significant beta-arrestin involvement.

SUMMARY OF THE INVENTION

The invention is directed to the above-mentioned need in the art and, in one embodiment, provides as a novel pharmacologically active agent an aryl-substituted N-alkyl indole having the molecular structure of formula (I)

(I)

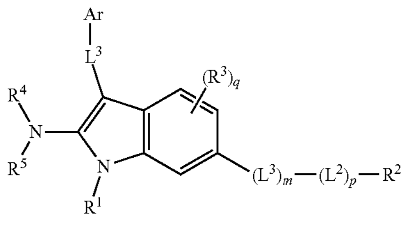

wherein:

m, p, and q are independently selected from zero and 1;

$L^1$ is selected from $C_1$-$C_3$ alkylene and $C_2$-$C_3$ alkenylene, and is optionally substituted with hydroxyl, $C_1$-$C_3$ alkoxy, or halo;

$L^2$ is selected from —(CO)— and —($SO_2$)—;

$L^3$ is selected from $C_2$-$C_3$ alkylene and $C_2$-$C_3$ alkenylene, and is optionally substituted with hydroxyl, $C_1$-$C_3$ alkoxy, or halo;

$R^1$ is H or $C_1$-$C_3$ alkyl;

$R^2$ is selected from $C_1$-$C_3$ alkyl, $C_2$-$C_3$ alkenyl, halogenated $C_1$-$C_3$ alkyl, halogenated $C_2$-$C_3$ alkenyl, hydroxyl, hydroxyl-substituted $C_1$-$C_3$ alkyl, $C_1$-$C_3$ alkoxy, cyano, amino, mono-$C_1$-$C_3$ alkyl-substituted amino, di-$C_1$-$C_3$ alkyl-substituted amino, and morpholinyl;

$R^3$ is selected from hydroxyl, $C_1$-$C_3$ alkoxy, and amino;

$R^4$ and $R^5$ are independently selected from H and $C_1$-$C_3$ alkyl or are linked to form an aliphatic N-heterocycle optionally substituted with one or two non-hydrogen substituents selected from $C_1$-$C_3$ alkyl, hydroxyl, and $C_1$-$C_3$ alkoxy, or wherein two non-hydrogen substituents on the aliphatic N-heterocycle are linked to form a bridged bicyclic moiety comprising a 1-, 2-, or 3-carbon atom bridge; and Ar is bicyclic N-heteroaryl bound to $L^3$ through a ring carbon atom and is optionally substituted with at least one substituent selected from hydroxyl, amido, mono-($C_1$-$C_3$ alkyl)amido, di-($C_1$-$C_3$ alkyl)amido, and $C_2$-$C_3$ acylamino.

As explained infra in Section (1) of the Detailed Description, reference to a compound of the invention or to any molecular structure herein includes not only the specified molecular entity but also pharmaceutically acceptable, pharmacologically active analogs of the entity, such as salts, esters, amides, prodrugs, conjugates, active metabolites, hydrates, solvates, complexes, prodrugs, and other such derivatives, analogs, and related compounds.

The aryl-substituted N-alkyl indoles provided herein exhibit potent efficacy in treatment of pain and inflammation compared to NSAIDs and morphine. However, in contrast to several other compounds currently contemplated for the treatment of pain and inflammation, such as a number of endocannabinoids, the aryl-substituted N-alkyl indoles of the invention little or no intoxicating activity. The aryl-substituted N-alkyl indoles of the invention are useful in numerous other methods as well, as will be detailed herein.

In some embodiments, an aryl-substituted N-alkyl indole of the invention exhibits moderate agonist activity at the $CB_1$ and/or $CB_2$ receptors. In some embodiments, an aryl-substituted N-alkyl indole of the invention is a biased $CB_1$ and/or $CB_2$ receptor agonist, selectively activating G protein signaling pathways relative to β-arrestin signaling pathways. In some embodiments, an aryl-substituted N-alkyl indole of the invention is a biased agonist of both the $CB_1$ and $CB_2$ receptors with minimal, if any, β-arrestin involvement. As such, unwanted side effects, particularly intoxicating effects, are avoided, following administration of the compound to a subject.

In another embodiment, the invention pertains to pharmaceutical formulations containing a therapeutically effective amount of at least one aryl-substituted N-alkyl indole as provided herein in combination with at least one pharmaceutically acceptable excipient. The formulations are generally "unit dosage" forms in which the therapeutically effective amount is suitable for a single dosage. The formulations may be immediate release or controlled release, and, if controlled release, are typically sustained release. The formulations may be prepared so as to be administered via any suitable route, e.g., oral, parenteral, transdermal, transmucosal (including intrarectal and intravaginal, via suppository or other suitable drug delivery platform), sublingual, by inhalation, via an implanted reservoir in a dosage form, and the like. For those compounds that are orally active, however, oral dosage forms are generally preferred, in which case the carrier is one that is suitable for oral ingestion. Oral formulations include solids, semi-solids, and liquids.

In an additional embodiment, pharmaceutical formulations are provided comprising a therapeutically effective amount of at least one aryl-substituted N-alkyl indole of the invention and at least one additional beneficial agent. Additional beneficial agents of interest include vitamins, minerals, amino acids, peptides, proteins, enzymes, co-enzymes, hormones, probiotics, fatty acids and other lipids, antioxidants, essential oils, fiber supplements, herbal supplements, botanicals, plant extracts, and pharmacologically active agents, e.g., anti-inflammatory and analgesic agents; it will be appreciated that any one compound may be encompassed by two or more of the foregoing categories.

The invention also provides a method for treating a condition, disease, or disorder in a mammalian subject by administering a therapeutically effective amount of a novel aryl-substituted N-alkyl indole of the invention or a pharmaceutical formulation comprising the aryl-substituted N-alkyl indole, wherein the "therapeutically effective amount" is an amount sufficient to treat the condition, disease, or disorder. Generally, the active agent is administered to a subject in a pharmaceutical formulation as described above, within the context of a predetermined dosing regimen.

In a related embodiment, the invention provides a method for administering a novel aryl-substituted N-alkyl indole as provided herein to an individual suffering from pain, endometriosis, primary dysmenorrhea, secondary premenstrual syndrome, uterine fibroid pain, menopausal symptoms, adenomyosis, polycystic ovary syndrome, alcoholism, anxiety, autism spectrum disorder, inflammatory bowel disease, celiac disease, systemic lupus erythematosus, Addison's disease, celiac disease, Graves' disease, Hashimoto thyroiditis, myasthenia gravis, psoriasis, Sjögren's disease, pernicious anemia, vasculitis, autoimmune hepatitis, and type 1 diabetes, burns, sarcomas, cardiac disorders, peripheral artery disease, cognitive pain, mild cognitive impairment, non-neurodegenerative dementia, multiple sclerosis, chronic inflammatory demyelinating polyneuropathy (CIDP), Guillain-Barre Syndrome, gingivitis, periodontitis, type 2 diabetes, glucose regulation, drug withdrawal, fibroses, acne, psoriasis, contact dermatitis, eczema, infectious skin ulcers, cellulitis, immunodeficiency, inflammation, ischemia, reduced fertility, limited fertility, fatty liver disease, cirrhosis, hepatitis, Metabolic Syndrome and any condition associated therewith, headaches, nausea, neurological disorders, neurodegenerative disorders, obesity, overweight, conditions caused by or associated with excess weight or obesity, osteoporosis, osteopenia, pelvic pain, attention deficit hyperactivity disorder (ADHD), bipolar disorder, depression, obsessive compulsive disorder (OCD), post-traumatic stress disorder (PTSD), psychosis, schizophrenia, respiratory disorders, seizure disorders, sleep apnea, insomnia, restless leg syndrome, REM sleep dysfunction, and stress.

Representative methods of particular interest include treatment of pain, regardless of origin, duration, or severity; treatment of women's health issues, e.g., endometriosis, dysmenorrhea, and the like; treatment of inflammatory arthritic disorders, inflammatory gastrointestinal disorders, and other disorders associated with or caused by inflammation; and a method for inducing weight loss in a subject and treating conditions caused by or otherwise associated with overweight or obesity. In some embodiments, an aryl-substituted N-alkyl indole of the invention is administered to a patient suffering from both pain and inflammation.

In a further embodiment of the invention, an opioid-sparing method is provided, i.e., a method for reducing the dose of an opioid needed to manage pain in a subject. Administration of opioid analgesics to control pain, as is well known, has significant risks, including addiction, overdose, and various unwanted side effects. In this embodiment, the invention provides an improved method to treat pain in a subject that offsets the aforementioned risks. The method comprises co-administering to a subject already receiving a therapeutically effective analgesic dose of an opioid, typically within a monotherapeutic dosage regimen, an opioid sparing dose of an aryl-substituted N-alkyl indole of the invention, thereby enabling a reduction in the therapeutically effective analgesic dose of the opioid.

In another embodiment, a method of opioid sparing in a subject in need of pain management is provided, where the method comprises co-administering to the subject an effective opioid-sparing dose of an aryl-substituted N-alkyl indole of the invention and an opioid analgesic.

In a related embodiment, a method is provided for transitioning a pain patient from an opioid dosing regimen to a dosing regimen comprising regular or as-needed administration of a therapeutically effective amount of an aryl-substituted N-alkyl indole of the invention.

In another embodiment, a method is provided for managing weight loss in a subject, wherein the method comprises co-administering to the subject an aryl-substituted N-alkyl indole of the invention and a glucagon-like peptide 1 receptor agonist (GLP-1 RA). In one embodiment, the method comprises administering an aryl-substituted N-alkyl indole of the invention to the subject at the beginning of an ongoing dosage regimen and co-administering the GLP-1 RA at a later point in the dosage regimen, wherein the GLP-1 RA is administered in an amount within or below the approved dosage range for the selected GLP-1RA. The method for managing weight loss extends to treatment of type 2 diabetes, Metabolic Syndrome, and other conditions, disorders, and diseases caused by or otherwise associated with obesity and excess weight.

DETAILED DESCRIPTION OF THE INVENTION

I. Definitions and Nomenclature

Figure 1:
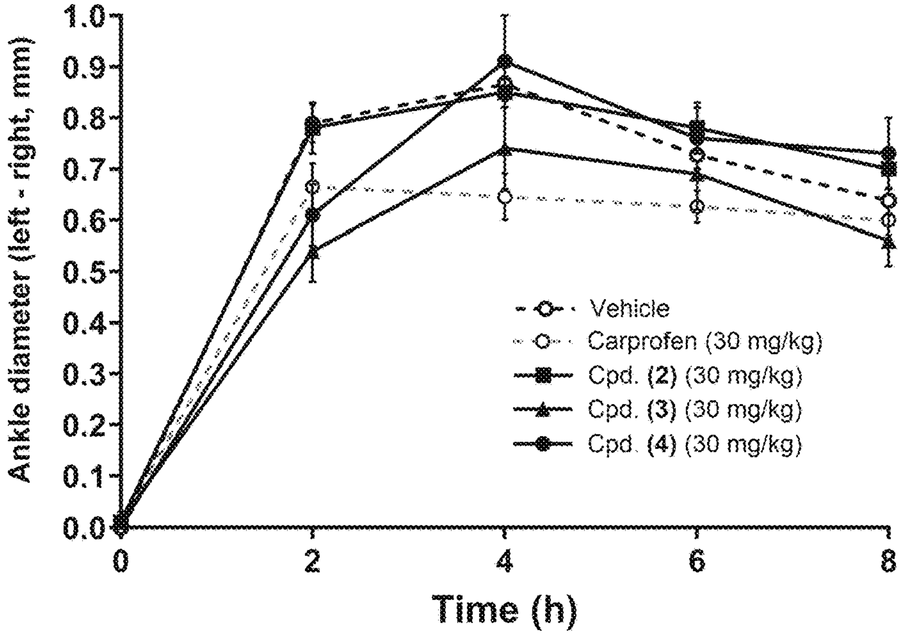
FIG. 1 is a graph indicating the efficacy of compounds (2), (3), and (4) in reducing carageenan-induced inflammation in mice and provides a comparison with carprofen and cannabinol, evaluated as described in Example 12.

Unless defined otherwise, all technical and scientific terms used herein have the meaning commonly understood by one of ordinary skill in the art to which the invention pertains. It is also to be understood that the terminology used herein is for the purpose of describing particular embodiments only and is not intended to be limiting. Specific terminology of particular importance to the description of the present invention is defined below.

In this specification and the appended claims, the singular forms "a," "an" and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable excipient" includes two or more excipients as well as a single carrier or excipient, and the like.

As used herein, the phrase "having the formula" or "having the structure" is not intended to be limiting and is used in the same way that the term "comprising" is used. In addition, unless otherwise indicated, the invention is not limited to specific synthetic methods, analogs, substituents, pharmaceutical formulations, formulation components, modes of administration, or the like, as such may vary.

The term "alkyl" as used herein refers to a branched or unbranched saturated hydrocarbon group typically although not necessarily containing 1 to 12 carbon atoms, such as methyl, ethyl, n-propyl, isopropyl, n-butyl, isobutyl, t-butyl, octyl, decyl, and the like, as well as cycloalkyl groups such as cyclobutyl, cyclopentyl, cyclohexyl, and the like. Generally, although again not necessarily, alkyl groups herein contain 1 to 6 carbon atoms, e.g., 1 to 3 carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the term "alkyl" includes linear, branched, cyclic, unsubstituted, substituted, and/or heteroatom-containing alkyl.

The term "alkylene" refers to a bivalent saturated aliphatic group containing 1 to 12 carbon atoms, and typically containing 1 to 6 carbon atoms or 1 to 3 carbon atoms. Unless otherwise indicated, the term "alkylene" includes substituted alkylene and/or heteroatom-containing alkylene.

The term "alkenyl" as used herein refers to a linear, branched or cyclic hydrocarbon group of 2 to 12 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to 6 carbon atoms, most typically 2 or 3 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" refers to a bivalent aliphatic group containing 2 to 6 carbon atoms and one carbon-carbon double bond, and typically contains 2 or 3 carbon atoms. Unless otherwise indicated, the term "alkenylene" includes substituted alkenylene and/or heteroatom-containing alkylene.

The term "alkoxy" as used herein intends an alkyl group bound through a single, terminal ether linkage; that is, an "alkoxy" group may be represented as —O-alkyl where alkyl is as defined above. Generally, the alkoxy groups herein contain 1 to 6 carbon atoms or 1 to 3 carbon atoms, and therefore include, for example, methoxy, ethoxy, n-propoxy, isopropoxy, t-butyloxy, etc. Preferred lower alkoxy substituents contain 1 to 3 carbon atoms, and particularly preferred such substituents contain 1 or 2 carbon atoms (i.e., methoxy and ethoxy). The terms "alkenyloxy" and "alkynyloxy" are defined in an analogous manner.

The term "aryl" as used herein, and unless otherwise specified, refers to an aromatic moiety or substituent containing a single aromatic ring or multiple aromatic rings that are fused together, directly linked, or indirectly linked (such that the different aromatic rings are bound to a common group such as a methylene or ethylene moiety). Aryl groups herein generally contain 3 to about 24 carbon atoms, most typically 3 to 14 carbon atoms. Exemplary aryl groups contain one aromatic ring or two fused or linked aromatic rings, e.g., phenyl, naphthyl, biphenyl, diphenylether, diphenylamine, benzophenone, and the like. Typical aryl groups herein are monocyclic 5-membered and 6-membered rings, e.g., substituted or unsubstituted phenyl or cyclopentyl. "Substituted aryl" refers to an aryl moiety substituted with one or more substituent groups, and the terms "heteroatom-containing aryl" and "heteroaryl" refer to an aryl moiety as defined above in which at least one carbon atom is replaced with a heteroatom, as will be described in further detail infra. If not otherwise indicated, the term "aryl" includes unsubstituted aryl, substituted aryl, unsubstituted heteroaryl, and substituted heteroaryl.

The term "cyclic" refers to alicyclic or aromatic substituents that may or may not be substituted and/or heteroatom containing, and that may be monocyclic, bicyclic, or polycyclic.

The term "alicyclic" is used in the conventional sense to refer to an aliphatic cyclic moiety, as opposed to an aromatic cyclic moiety, and may be monocyclic, bicyclic, or polycyclic, and, if bicyclic or polycyclic, may be bridged, linked, or fused.

The terms "halo" and "halogen" are used in the conventional sense to refer to a chloro, bromo, fluoro, or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage, or substituent in which one or more carbon atoms are replaced with an atom other than carbon, e.g., nitrogen, oxygen, sulfur, phosphorus, or silicon, typically nitrogen, oxygen, or sulfur, preferably nitrogen or oxygen. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyridinyl, isoquinolinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include functional groups and hydrocarbyl moieties (including, but not limited to, the hydrocarbyl moieties defined above).

Functional groups that may represent substituents in the substituted molecular structures and segments thereof include, without limitation: halo (Cl, Br, I, F), hydroxyl, sulfhydryl, $C_1$-$C_{12}$ alkoxy (particularly $C_1$-$C_6$ alkoxy, e.g., $C_1$-$C_3$ alkoxy), $C_2$-$C_{12}$ alkoxyalkyl (particularly $C_2$-$C_6$ alkoxyalkyl, e.g., $C_2$-$C_3$ alkoxyalkyl), $C_2$-$C_{12}$ alkenyloxy (particularly $C_2$-$C_6$ alkenyloxy, e.g., $C_2$-$C_3$ alkenyloxy), $C_4$-$C_{18}$ aryloxy, acyl (including $C_2$-$C_{12}$ alkylcarbonyl (—CO-alkyl), particularly $C_2$-$C_6$ alkylcarbonyl, e.g., $C_2$-$C_3$ alkylcarbonyl, and $C_3$-$C_{14}$ aryl-substituted carbonyl), acyloxy (—O-acyl), $C_2$-$C_{12}$ alkoxycarbonyl (—(CO)—O-alkyl, particularly —(CO)—O—$C_1$-$C_6$ alkylcarbonyl and —(CO)—O—$C_1$-$C_3$ alkylcarbonyl), $C_3$-$C_{14}$ aryloxy-substituted carbonyl (—(CO)—O—$C_3$-$C_{14}$ aryl), halocarbonyl (—CO)—X where X is halo), $C_2$-$C_{13}$ alkylcarbonato (—O—(CO)—O—$C_1$-$C_{12}$alkyl, e.g., —O—(CO)—O—$C_1$-$C_{16}$ alkyl), carboxyl (—COOH), carboxylato (—COO—), carbamoyl (—(CO)—$NH_2$), mono-($C_1$-$C_6$ alkyl)-substituted carbamoyl (—(CO)—NH($C_1$-$C_6$ alkyl), particularly —(CO)—NH($C_1$-$C_3$ alkyl)), di-($C_1$-$C_6$ alkyl)-substituted carbamoyl (—(CO)—N($C_1$-$C_6$ alkyl$)_2$, particularly —(CO)—NH($C_1$-$C_3$ alkyl$)_2$), mono-($C_3$-$C_{14}$ aryl)-substituted carbamoyl (—(CO)—NH-aryl), di-($C_3$-$C_{14}$ aryl)-substituted carbamoyl (—(CO)—N(aryl$)_2$), thiocarbamoyl (—(CS)—$NH_2$), carbamido (—NH—(CO)—$NH_2$), cyano (—C≡N), isocyano (—$N^+$≡$C^-$—), cyanato (—O—C≡N), isocyanato (—O—$N^+$≡$C^-$—), isothiocyanato (—S—C≡N), azido (—N═$N^+$═$N^-$—), formyl (—(CO)—H), thioformyl (—(CS)—H), amino (—$NH_2$), mono-($C_1$-$C_6$ alkyl)-substituted amino (particularly mono-($C_1$-$C_3$ alkyl)-substituted amino), di-($C_1$-$C_6$ alkyl)-substituted amino (particularly di-($C_1$-$C_3$ alkyl)-substituted amino), mono-($C_3$-$C_{14}$ aryl)-substituted amino, di-($C_3$-$C_{14}$ aryl)-substituted amino, $C_2$-$C_{12}$ alkylamido (—NH—(CO)-alkyl) (particularly $C_2$-$C_7$ alkylamido (—NH—(CO)—$C_1$-$C_6$ alkyl), e.g., —NH—(CO)—$C_1$-$C_3$ alkyl), $C_3$-$C_{14}$ arylamido (—NH—(CO)-aryl), imino (—CR═NH where R═hydrogen, alkyl, aryl, alkaryl, aralkyl, etc.), alkylimino (—CR═N(alkyl) where R is as before, arylimino (—CR═N(aryl), where R is as before), nitro (—$NO_2$), nitroso (—NO), sulfo (—$SO_2$—OH), sulfonato (—$SO_2$—O—), $C_1$-$C_{12}$ alkylsulfanyl (—S-alkyl; also termed "alkylthio"), arylsulfanyl (—S-aryl; also termed "arylthio"), alkylsulfinyl (—(SO)-alkyl), arylsulfinyl (—(SO)-aryl), alkylsulfonyl (—$SO_2$-alkyl), arylsulfonyl (—$SO_2$-aryl), phosphono (—P(O)(OH$)_2$), phosphonato (—P(O)(O—$)_2$), phosphinato (—P(O)(O—)), phospho (—$PO_2$), and phosphino (—$PH_2$), wherein alkyl, alkenyl, aryl, etc., are as defined previously.

The aforementioned functional groups may, if a particular group permits, be further substituted with one or more additional functional groups or with one or more hydrocarbyl moieties such as those specifically enumerated above, and the term "functional group" encompasses all such instances.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

The numbering systems typically applied to certain nitrogen heterocycles as well as to analogous substituents and compounds herein follow convention. For example, the numbering used herein for indole (and indolyl substituents or cores), isoquinoline (and isoquinolinyl moieties), and morpholine (including morpholinyl substituents) are shown below:

indole or indolyl numbering convention:

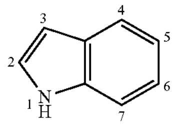

isoquinoline or isoquinolinyl numbering convention:

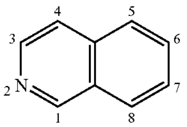

morpholine or morpholinyl numbering convention:

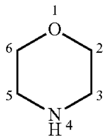

The term "protected" to refer to a functional group means that the group is in modified form to preclude undesired side reactions at the protected site. Suitable protecting groups for the compounds of the present invention will be recognized from this description taking into account the level of skill in the art, and with reference to standard textbooks, such as Greene et al., Protective Groups in Organic Synthesis (New York: Wiley, 1991). A "protected" compound refers to a compound in which one or more functional groups are protected.

The terms "active agent," "pharmacologically active agent," and "drug" are used interchangeably herein to refer to a chemical compound that, when administered to an organism (human or animal) induces a desired pharmacological effect. Included are derivatives and analogs of those compounds or classes of compounds that also induce the desired effect. When referring to an aryl-substituted N-alkyl indole of the invention as an active agent, then, it is intended that the compound encompass not only the specified molecular entity but also its pharmaceutically acceptable, pharmacologically active analogs, including, but not limited to, salts, esters, amides, prodrugs, conjugates, active metabolites, racemic mixtures, hydrates, solvates, complexes, prodrugs, and other such derivatives, analogs, and related compounds.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, "treating" a subject or patient with a compound of the invention includes prevention of a particular disorder or adverse physiological event in a susceptible individual as well as treatment of a clinically symptomatic individual by inhibiting or causing regression of a disorder or disease. The terms "condition," "disorder," and "disease" are used interchangeably herein as adverse physiological states that are treatable with the aryl-substituted N-alkyl indoles of the invention.

The terms "subject" and "patient" are used interchangeably herein to refer to the individual to whom an aryl-substituted N-alkyl indole of the invention is administered, and while usually indicating a human individual, the terms may also refer to a non-human mammal.

By the terms "effective amount" and "therapeutically effective amount" of an aryl-substituted N-alkyl indole of the invention is meant a nontoxic but sufficient amount of the compound to provide the desired effect in a particular context, depending, for instance, on the indication being addressed, the mode of administration, the medical history of the subject to whom the compound is administered, the subject's weight, age, and general health, as well as the judgment of the prescribing physician. Examples of suitable ranges for the therapeutically effective amount are provided in Section III of this Detailed Description.

The term "dosage form" denotes any form of a pharmaceutical formulation that contains a therapeutically effective amount of the active agent.

"Carriers" or "vehicles" as used herein refer to subsets of the general class of pharmaceutically acceptable excipients. Carriers and vehicles useful herein include any such materials known in the art, e.g., any liquid, gel, solvent, liquid diluent, solubilizer, or the like, which is nontoxic and does not interact with other components of the formulation in a deleterious manner.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein includes sustained release and delayed release formulations.

(66) The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period.

(67) By "pharmaceutically acceptable" is meant a material that is not biologically or otherwise undesirable, i.e., the material may be incorporated into a pharmaceutical formulation administered to a subject without causing any undesirable biological effects or interacting in a deleterious manner with any of the other components of the formulation in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration and/or designated GRAS ("Generally Recognized as Safe").

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

II. The Novel Aryl-Substituted N-Alkyl Indoles

In one embodiment, the invention provides an aryl-substituted N-alkyl indole having the molecular structure of formula (I)

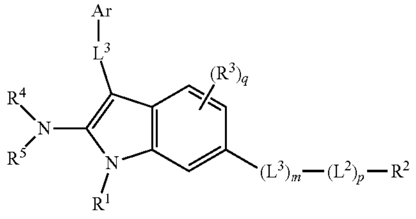

(I)

wherein m, p, q, $L^1$, $L^2$, $L^3$, $R^1$ through $R^5$, and Ar are as follows:

The integers m, p, and q are independently selected from zero and 1, such that $L^1$, $L^2$, and $R^3$ may or may not be present in the molecular structure.

$L^1$ is a linking moiety selected from $C_1$-$C_3$ alkylene and $C_2$-$C_3$ alkenylene, and is optionally substituted with hydroxyl, $C_1$-$C_3$ alkoxy, or halo. In some embodiments, $L^1$ is $C_1$-$C_3$ alkylene optionally substituted with hydroxyl or fluoro. In some embodiments, $L^1$ is unsubstituted $C_1$-$C_3$ alkylene, e.g., $-CH_2-$, $-CH_2CH_2-$, $-CH(CH_3)-$, etc. In other embodiments, as noted above, m is zero and $L^1$ is absent.

$L^2$ is selected from $-(CO)-$ and $-(SO_2)-$. In some embodiments, $L^2$ is $-(CO)-$. In other embodiments, p is zero, such that $L^2$ is absent.

$L^3$ is selected from $C_2$-$C_3$ alkylene and $C_2$-$C_3$ alkenylene, and is optionally substituted with hydroxyl, $C_1$-$C_3$ alkoxy, or halo. In some embodiments, $L^3$ is unsubstituted $C_2$-$C_3$ alkylene, e.g., $L^3$ may be an ethylene ($-CH_2CH_2-$) linkage.

$R^1$ is H or $C_1$-$C_3$ alkyl, and is typically methyl.

$R^2$ is selected from $C_1$-$C_3$ alkyl, $C_2$-$C_3$ alkenyl, halogenated $C_1$-$C_3$ alkyl, halogenated $C_2$-$C_3$ alkenyl, hydroxyl, hydroxyl-substituted $C_1$-$C_3$ alkyl, $C_1$-$C_3$ alkoxy, cyano, amino, mono-$C_1$-$C_3$ alkyl-substituted amino, di-$C_1$-$C_3$ alkyl-substituted amino, and morpholinyl.

$R^3$ is selected from hydroxyl, $C_1$-$C_3$ alkoxy, and amino. In some embodiments, $R^3$ is hydroxyl. In other embodiments, q is zero, such that $R^3$ is absent.

$R^4$ and $R^5$ are independently selected from H and $C_1$-$C_3$ alkyl or are linked to form an aliphatic N-heterocycle optionally substituted with one or two non-hydrogen substituents selected from $C_1$-$C_3$ alkyl, hydroxyl, and $C_1$-$C_3$ alkoxy, or wherein two non-hydrogen substituents on the aliphatic N-heterocycle are linked to form a bridged bicyclic moiety comprising a 1-, 2-, or 3-carbon atom bridge. In some embodiments, $R^4$ and $R^5$ are linked to form an unsubstituted morpholinyl ring. In some embodiments, $R^4$ and $R^5$ are linked to form a morpholinyl ring substituted with one or two hydroxyl groups. In some embodiments, $R^4$ and $R^5$ are linked to form a morpholinyl ring substituted with one or two methyl groups. In some embodiments, $R^4$ and $R^5$ are linked to form a morpholinyl ring with two carbon atoms linked through a 1-, 2-, or 3-carbon atom bridge to form a bicyclic structure.

Ar is bicyclic N-heteroaryl bound to $L^3$ through a ring carbon atom and is optionally substituted with at least one substituent selected from hydroxyl, amido, mono-($C_1$-$C_3$ alkyl)amido, di-($C_1$-$C_3$ alkyl)amido, and $C_2$-$C_3$ acylamino. The nitrogen atom of Ar may be adjacent to the carbon atom bound to $L^3$, such that Ar is a 1-isoquinolinyl substituent, or the nitrogen atom of Ar may be elsewhere in the molecular structure. Bicyclic N-heteroaryl groups include, by way of example, indolyl, quinolinyl, isoquinolinyl, tetrahydroquinolinyl, tetrahydroisoquinolinyl, benzimidazolyl, purinyl, imidazopyridinyl, imidazopyrimidinyl, triazolopyridinyl, and the like, any of which may be substituted as previously described. The aromatic substituent Ar may also be partially aromatic, i.e., comprised of an aromatic moiety fused or linked to a nonaromatic cyclic group, such as is the case, for instance, in 4-tetraisohydroquinolyl, dihydroindolyl, and the like. In some embodiments, Ar is unsubstituted isoquinolinyl. In other embodiments, Ar is 4-tetraisohydroquinolyl.

When p is 1 and $L^2$ is —(CO)—, representative compounds have the molecular structures of (I-A) and (I-B):

(I-A)

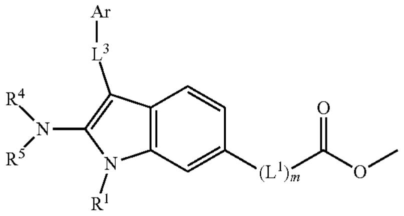

(I-B)

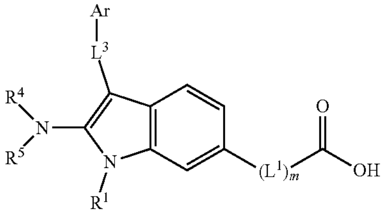

Other representative embodiments having the molecular structure of formula (I) are those wherein p is zero, such that $L^2$ is absent, for instance compounds (I-C) and (I-D):

*I-C)

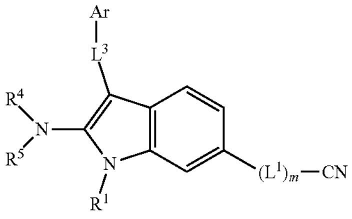

-continued (I-D)

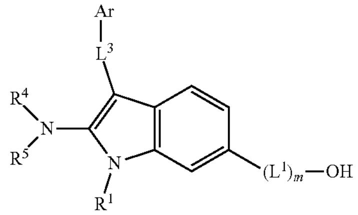

In some embodiments, referring to the definitions pertaining to structural formula (I):

m is 1;

p and q are zero;

$L^1$ is $C_1$-$C_3$ alkylene;

$L^3$ is —$CH_2CH_2$—;

$R^1$ is $C_1$-$C_3$ alkyl;

$R^2$ is cyano;

$R^4$ and $R^5$ are linked to form a morpholinyl group, wherein the morpholinyl group is optionally substituted with one or two substituents that are $C_1$-$C_3$ alkyl groups or with two substituents that together form a bridged bicyclic moiety having a 2-carbon atom bridge; and Ar is selected from quinolinyl, isoquinolinyl, tetrahydroquinolinyl, and tetrahydroisoquinolinyl, and is optionally substituted with a hydroxyl, amido, methylamido, dimethylamido, or acetylamino group.

Such compounds have the structure of formula (II)

(II)

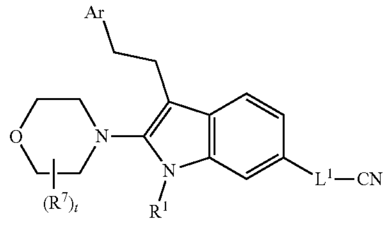

wherein t is zero, 1, or 2; $R^6$ is hydroxyl, amido, methylamido, dimethylamido, or acetylamino; and $R^7$ is $C_1$-$C_3$ alkyl.

In one subset of these compounds, $L^1$ is —CH—, $R^1$ is methyl, and Ar is 1-isoquinolinyl optionally substituted with a hydroxyl, methylamido, or acetylamino group. These compounds have the molecular structure of formula (II-A)

(II-A)

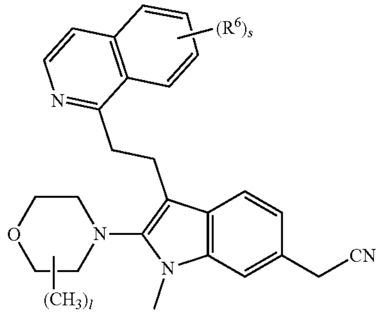

wherein s is zero, 1, or 2, and the $R^6$ substituent may be on either ring of the isoquinolinyl substituent, or there may be identical or different $R^6$ substituents on both rings. In some embodiments, s in the structure of formula (II-A) is 1. In some embodiments, s is zero. In some embodiments, t is 1. In some embodiments, t is zero.

In other embodiments, referring to structural formula (I):

m is zero or 1;

p is 1;

q is zero;

$L^1$ is $C_1$-$C_3$ alkylene;

$L^3$ is $—CH_2CH_2—$;

$R^1$ is $C_1$-$C_3$ alkyl;

$R^2$ is selected from hydroxyl, amino, and $C_1$-$C_3$ alkoxy;

$R^4$ and $R^5$ are linked to form a morpholinyl group optionally substituted with one or two substituents that are $C_1$-$C_3$ alkyl groups or optionally substituted with two substituents that together form a bridged bicyclic moiety having a 2-carbon atom bridge; and Ar is selected from quinolinyl, isoquinolinyl, tetrahydroquinolinyl, and tetrahydroisoquinolinyl, any of which is optionally substituted with a hydroxyl, amido, methylamido, dimethylamido, or acetylamino group.

These compounds have the structure of formula (III)

(III)

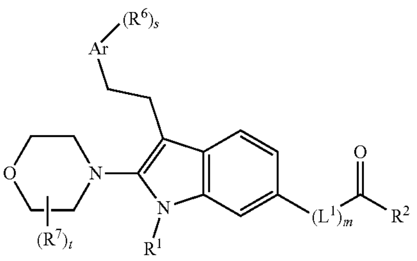

wherein s and t are independently selected from zero, 1, and 2; $R^6$ is hydroxyl, amido, methylamido, dimethylamido, or acetylamino; and $R^7$ is $C_1$-$C_3$ alkyl.

In one subset of these compounds, m is 1, $L^1$ is $—CH_2—$, $R^1$ is methyl, $R^2$ is amino, and Ar is 1-isoquinolinyl optionally substituted with a hydroxyl, methylamido, or acetylamino group. These compounds have the molecular structure of formula (III-A)

(III-A)

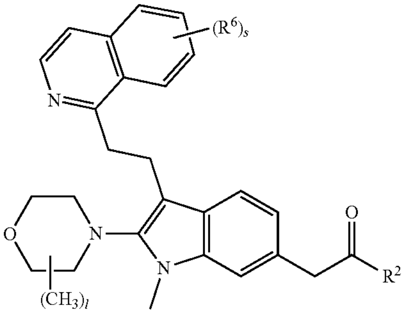

wherein the $R^6$ substituent may be on either ring of the isoquinolinyl substituent, or there may be identical or different $R^6$ substituents on both rings. In some embodiments, s in the structure of formula (III-A) is 1. In some embodiments, s is zero. In some embodiments, t is 1. In some embodiments, t is zero.

Specific representative aryl-substituted N-alkyl indoles of the invention include, without limitation, the following compounds:

(1)

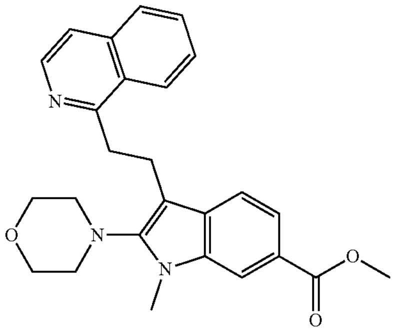

(2)

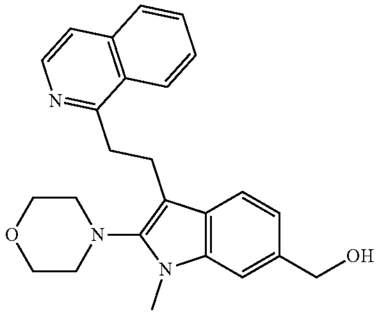

(3)

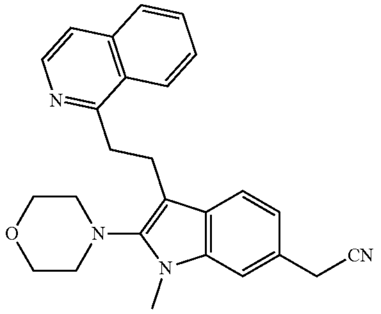

(4)

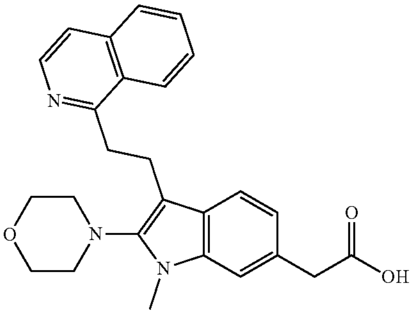

-continued
(5)
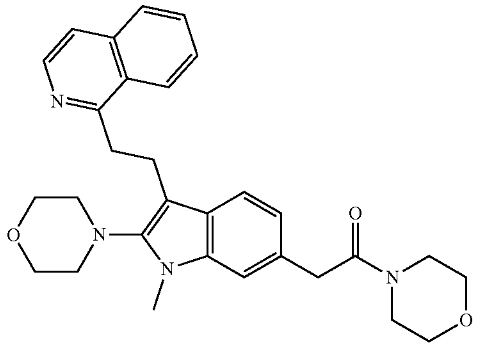
(6)
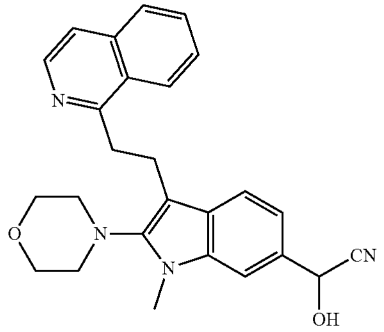
(7)
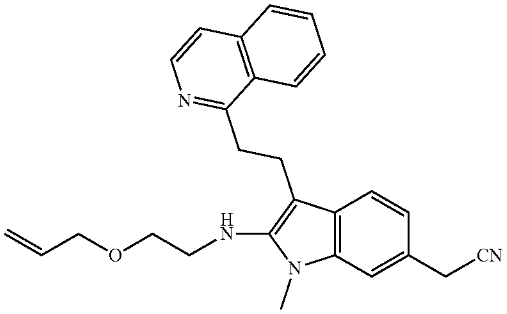
(8)
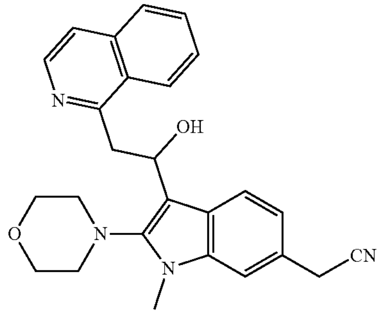
(9)
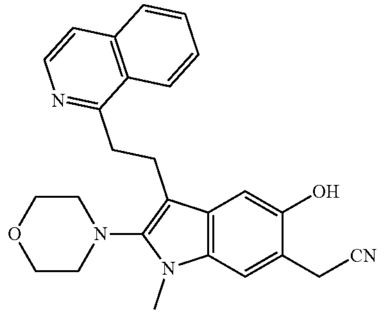
-continued
(10)
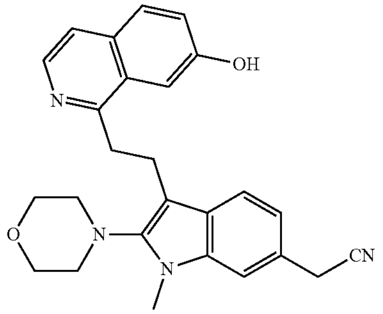
(11)
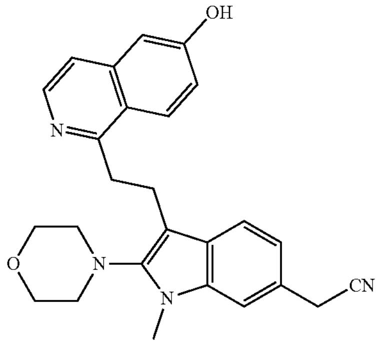
(12)
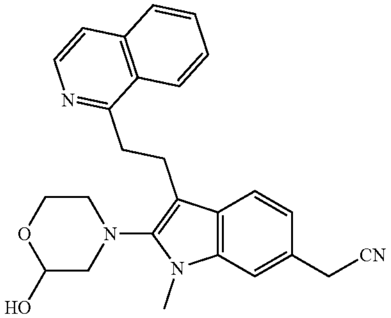
(13)
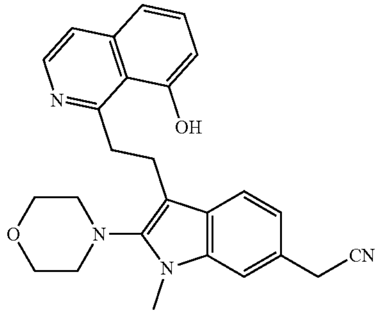

-continued
(14)
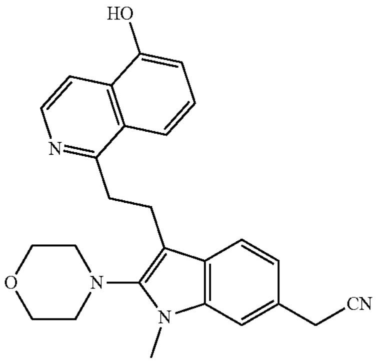
(15)
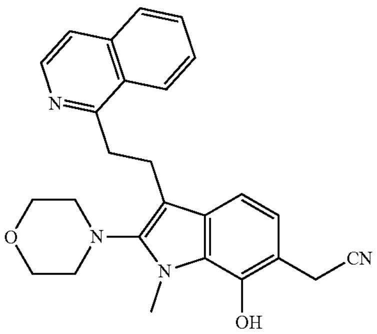
(16)
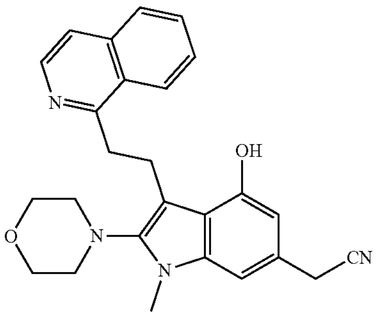
(17)
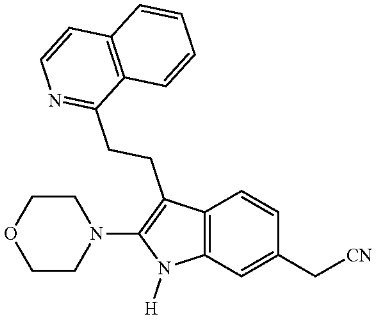
-continued
(18)
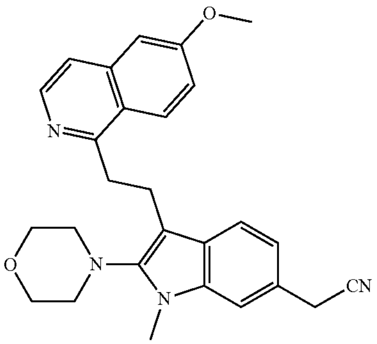
(19)
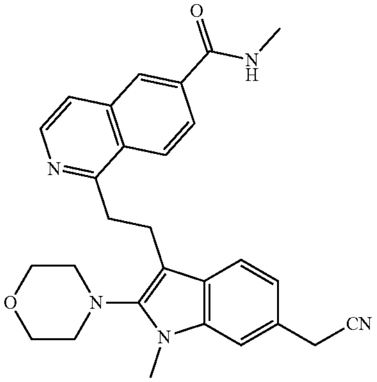
(20)
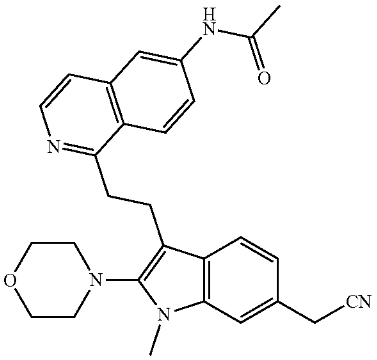
(21)
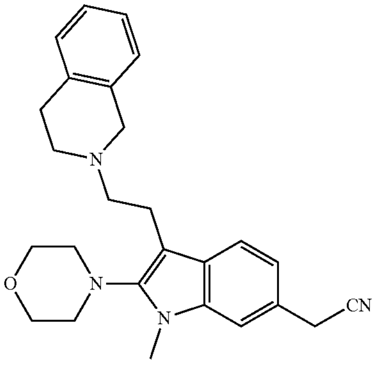

-continued (22)

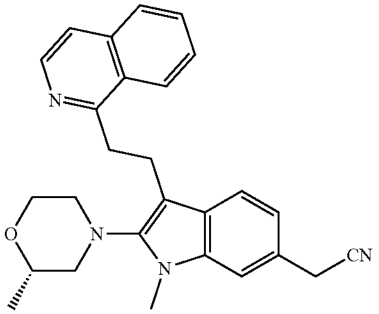

(23)

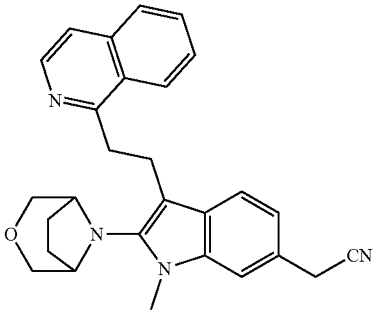

(24)

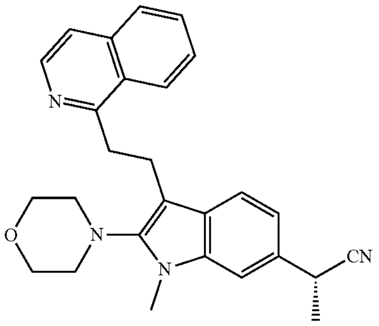

(25)

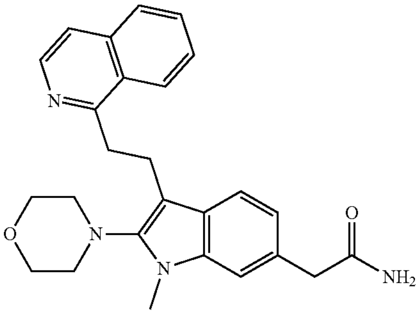

Compounds of formula (I) may be readily synthesized using the methods set forth in the examples herein, augmented, if necessary, by the inherent knowledge of one of ordinary skill in the art of synthetic organic chemistry and/or by reference to the pertinent texts and literature.

III. Pharmaceutical Formulations, Dosage Forms, and Modes of Administration

Pharmaceutical formulations suitable for administration of an aryl-substituted N-alkyl indole of the invention are formulations wherein the aryl-substituted N-alkyl indole, as a pharmacologically active agent, is contained in a therapeutically effective amount, i.e., in an amount or concentration effective to achieve its intended purpose. Typically, the therapeutically effective amount is a unit dose, as explained infra. The active agent may be in the form of a reaction product composition, but more typically is in isolated, purified form.

Determination of a therapeutically effective amount for a particular aryl-substituted N-alkyl indole is within the capability of those skilled in the art. Generally, toxicity and therapeutic efficacy of a compound or formulation described herein can be determined by standard pharmaceutical procedures in cell cultures or experimental animals, e.g., procedures used for determining the maximum tolerated dose (MTD), the ED50, which is the effective dose to achieve 50% of maximal response, and the therapeutic index (TI), which is the ratio of the MTD to the ED50. Compounds and formulations with high TIs are the more preferred compounds and formulations herein, and preferred dosage regimens are those that maintain plasma levels of the active agents at or above a minimum concentration for a predetermined time period to maintain the desired therapeutic effect. Dosage will, of course, also depend on a number of factors, including the particular aryl-substituted N-alkyl indole, the formulation type, the site of intended delivery, the route of administration, and other pertinent factors known to the prescribing physician.

Administration of an aryl-substituted N-alkyl indole of the invention may be carried out using any appropriate mode of administration. Thus, administration can be, for example, oral, parenteral, transdermal, transmucosal (including intrarectal and intravaginal, via suppository, ointment, cream, or the like), sublingual, by inhalation, or via an implanted reservoir in a dosage form. The term “parenteral” as used herein is intended to include subcutaneous, intravenous, and intramuscular injection. Depending on the intended mode of administration, the pharmaceutical formulation containing the aryl-substituted N-alkyl indole may be a solid, semi-solid or liquid, such as, for example, a tablet, a capsule, a caplet, a gummy, a lozenge (e.g., a troche), a solution (e.g., an elixir or syrup), a suspension (e.g., an emulsion), a suppository, granules, pellets, beads, a powder, or the like, preferably, although not necessarily, in unit dosage form suitable for single administration of a precise dosage. As is understood in the field of pharmaceutical formulation, a “unit dose” or “unit dosage” refers to the amount of an active agent in a single dose to be administered to a subject, with a “unit dosage form” referring to a dosage form that contains a unit dosage. Suitable pharmaceutical formulations may be prepared using conventional methods known to those in the field of pharmaceutical formulation and described in the pertinent texts and literature, e.g., in Remington: The Science and Practice of Pharmacy, cited supra.

For solid compositions, conventional nontoxic solid carriers include, by way of example, pharmaceutical grades of mannitol, lactose, starch, magnesium stearate, sodium saccharin, talc, cellulose, glucose, sucrose, magnesium carbonate, and the like. Liquid pharmaceutically administrable formulations can, for example, be prepared by dissolving, dispersing, etc., an active agent as described herein and one or more optional pharmaceutical adjuvants as excipients, such as, for example, water, saline, aqueous dextrose, glycerol, ethanol, and the like, to thereby form a solution or suspension. If desired, the pharmaceutical formulation to be administered may also contain minor amounts of nontoxic auxiliary substances such as wetting or emulsifying agents, pH buffering agents and the like, for example, sodium acetate, sorbitan mono-laurate, triethanolamine sodium acetate, triethanolamine oleate, etc. See Remington's Pharmaceutical Sciences, referenced above.

For those aryl-substituted N-alkyl indoles that are orally active, oral dosage forms are generally preferred, and include, without limitation, tablets, capsules, caplets, gummies, lozenges (e.g., troches), suspensions (e.g., emulsions), oral gels, and solutions (e.g., elixirs and syrups), and may also comprise a plurality of dispersible granules, beads, powders, or pellets that may or may not be encapsulated. Preferred oral dosage forms are tablets, capsules, gummies, and solutions.

Tablets may be manufactured using standard tablet processing procedures and equipment. Direct compression and granulation techniques are preferred. In addition to the active agent, tablets will generally contain inactive, pharmaceutically acceptable carrier materials such as binders (e.g., starches, acacia, alginates, carboxymethylcellulose, polyvinyl pyrrolidone, and the like), lubricants (e.g., stearic acid or stearates such as magnesium stearate and calcium stearate), disintegrants (e.g., starches, clays, celluloses, etc.), fillers (e.g., silicon dioxide, kaolin, microcrystalline cellulose, anhydrous lactose, sorbitol, etc., as is known in the art), stabilizers, surfactants, coloring agents, antioxidants, preservatives, and the like. Tablets may be prepared so as to be swallowed intact, or they may contain disintegrants, taste-masking agents, or the like, so as to be rendered chewable.

Capsules are also suitable oral dosage forms for those aryl-substituted N-alkyl indoles that are orally active, in which case the analog-containing formulation may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Pharmaceutical gummies are also suitable dosage forms for orally administering an aryl-substituted N-alkyl indole of the invention. As is known in the art, gummies are comprised of a gelling agent, i.e., gelatin and/or a gelatin equivalent such as pectin or xanthan gum; a sweetener, which may be sugar-based (e.g., sucrose, glucose syrup, etc.) or a non-sucrose natural or artificial sweetener (e.g., sucralose, sorbitol, erythritol, stevia, corn syrup, agave syrup, etc.); a flavoring; a colorant; and generally, although not necessarily, one or more optional excipients in addition to the foregoing, such as stabilizers, solubilizers, taste-masking agents, anti-oxidants, preservatives, and the like. A gummy formulation of the invention, then, comprises a therapeutically effective amount of aryl-substituted N-alkyl indole of the invention; gelatin and/or a gelatin equivalent; a sweetener; a flavoring; a colorant; and, optionally, one or more of the excipients mentioned above. An example of a gummy formulation for administering an aryl-substituted N-alkyl indole of the invention comprises the following components: 0.25 wt. % to 20 wt. % of the aryl-substituted N-alkyl indole; 2.5 wt. % to 10 wt. % gelling agent; and 10 wt. % to 60 wt. % sweetener, with water representing the remainder of the formulation. For example, a gummy formulation of the invention may comprise 0.25 wt. % to 15 wt. % of the aryl-substituted N-alkyl indole (e.g., 0.25 wt. % to 5.0 wt. %); 3.0 wt. % to 7.5 wt. % gelling agent; and 20 wt. % to 50 wt. % sweetener. Optionally, the formulation may also include one or more excipients that can serve to enhance taste, appearance, stability, and overall product quality. Such excipients include, without limitation, flavoring agents, colorants, preservatives, emulsifiers, and the like.

Some dosage forms, whether tablets, capsules, caplets, lozenges, particulates, implants, or suppositories, may, if desired, be formulated so as to provide for controlled release of the active agent. A preferred form of controlled release herein is sustained release, so as to provide gradual release of the aryl-substituted N-alkyl indole from the dosage form over an extended time period, e.g., 12-36 hours, 12-24 hours, or the like. Generally, as will be appreciated by those of ordinary skill in the art, sustained release dosage forms are formulated by dispersing the selected active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations for parenteral administration of the aryl-substituted N-alkyl indole include sterile aqueous and non-aqueous solutions, suspensions, and emulsions. Injectable aqueous solutions contain the aryl-substituted N-alkyl indole in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations, including formulations for intravenous and intramuscular administration, are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

Suppositories can also be prepared to administer an aryl-substituted N-alkyl indole of the invention vaginally or rectally. As is known in the art, suppositories are prepared by mixing an active agent with a suitable non-irritating base material that is solid at ordinary (e.g., storage) temperatures but liquid at internal body temperature, so that the suppository melts and begins releasing the active agent therein after administration. The base material makes up the majority of the suppository's weight, which is typically in the range of 1 g to 4 g, and may be an oleaginous base, e.g., cocoa butter, a hydrogenated vegetable oil, a synthetic triglyceride, etc.; a hydrophilic water-soluble or water-miscible base, e.g., glycerinated gelatin or polyethylene glycols; or a water-dispersible base, typically an oleaginous base mixed with one or more surfactants to increase hydrophilicity. Generally, suppositories additionally contain at least one excipient, typically selected from suspending agents, emulsifying agents, stiffening agents, preservatives, lubricants, and the like. Depending on the particular active agent and the selected suppository base and excipients, the active agent will generally represent in the range of 1 wt. % to 25 wt. % of the suppository, more typically in the range of 2.5 wt. % to 15 wt. %.

An example of a suppository formulated with an aryl-substituted N-alkyl indole of the invention is an intravaginal suppository, formulated to treat, for instance, endometriosis or a symptom thereof, wherein the suppository comprises 0.25 wt. % to 50 wt. %, 0.25 wt. % to 30 wt. %, 0.25 wt. % to 20 wt. %, 0.25 wt. % to 10 wt. %, 0.25 wt. % to 5 wt. %, 0.5 wt. % to 50 wt. %, 0.5 wt. % to 30 wt. %, 0.5 wt. % to 20 wt. %, 0.5 wt. % to 10 wt. %, 0.5 wt. % to 5 wt. %, 1.0 wt. % to 50 wt. %, 1.0 wt. % to 30 wt. %, 1.0 wt. % to 20 wt. %, 1.0 wt. % to 10 wt. %, 1.0 wt. % to 5 wt. %, 2.5 wt. % to 50 wt. %, 2.5 wt. % to 30 wt. %, 2.5 wt. % to 20 wt. %, 2.5 wt. % to 10 wt. %, 2.5 wt. % to 5 wt. %, of aryl-substituted N-alkyl indole as provided herein, and 15 wt. % to 75 wt. % suppository base as provided above, with one or more excipients making up the remainder of the dosage form.

An aryl-substituted N-alkyl indole as provided herein can also be administered intravaginally in the treatment of endometriosis or other conditions using a different type of physical form, e.g., an ointment, cream, gel, liquid, or the like. Ointments, as is well known in the art of pharmaceutical formulation, are semisolid preparations that are typically based on petrolatum or other petroleum derivatives. The specific ointment base to be used is one that will provide for optimum drug delivery. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information. Creams, including creams for intravaginal administration of an aryl-substituted N-alkyl indole of the invention, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant. The concentration of the aryl-substituted N-alkyl indole in the ointment or cream is present within the same ranges as the concentration of the analog in a suppository, provided above.

The aryl-substituted N-alkyl indole may, in addition, be administered through the skin using conventional transdermal drug delivery systems, wherein the active agent is contained within a laminated structure that serves as a drug delivery device to be affixed to the skin. In such a structure, the drug formulation is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer to facilitate passage of the active agent through the skin.

In addition, the aryl-substituted N-alkyl indole may be formulated in a depot preparation for controlled release of the active agent, preferably sustained release over an extended time period. These sustained release dosage forms are generally administered by implantation (e.g., subcutaneously or by intramuscular injection).

The aryl-substituted N-alkyl indole can also be formulated for inhalation, e.g., as a solution in saline, as a dry powder, or as an aerosol. Administration may be via the intranasal route or via oral inhalation. A pharmaceutical formulation for delivery to the lungs via oral inhalation can also be a dry powder formulation, such as may comprise nanoparticle-sized solid particles containing the aryl-substituted N-alkyl indole and suitable dry powder excipients, for example, lactose monohydrate, magnesium stearate, mannitol, or the like. Suitable dry powder components and inhaler types are described, inter alia, by de Boer (2017) *Expert Opin Drug Deliv.* 14(4): 499-512, and U.S. Patent Publication No. 2009/00004279 to Hofmann et al., both incorporated by reference herein.

A suitable unit dose of the aryl-substituted N-alkyl indole for a 70 kg human is typically in the range of 5 mg to 500 mg, e.g., 5 mg to 250 mg, 5 mg to 100 mg, 5 mg to 75 mg, 5 mg to 60 mg, 5 mg to 50 mg, 5 mg to 30 mg, 5 mg to 15 mg, 10 mg to 150 mg, 10 mg to 100 mg, 10 mg to 75 mg, 10 mg to 60 mg, 10 mg to 50 mg, 10 mg to 30 mg, 20 mg to 200 mg, 20 mg to 100 mg, or 20 mg to 50 mg, with a typical daily dose in the range of about 10 mg to 1000 mg, 10 mg to 500 mg, 10 mg to 200 mg, e.g., 10 mg to 150 mg, 10 mg to 120 mg, 10 mg to 100 mg, 10 mg to 60 mg, 10 mg to 30 mg, 20 mg to 300 mg, 20 mg to 200 mg, 20 mg to 150 mg, 20 mg to 120 mg, 20 mg to 100 mg, 20 mg to 60 mg, 40 mg to 400 mg, 40 mg to 200 mg, or 40 mg to 100 mg.

Depending on the type of formulation or dosage form, the amount of the aryl-substituted N-alkyl indole therein will generally be in the range of 0.25 wt. % to 99 wt. %, 0.25 wt. % to 75 wt. %, 0.25 wt. % to 50 wt. %, 0.25 wt. % to 20 wt. %, 1 wt. % to 95 wt. %, e.g., 5 wt. % to 95 wt. %, 5 wt. % to 90 wt. %, 10 wt. % to 80 wt. %, 15 wt. % to 75 wt. %, and so forth.

For nonsolid formulations specifically, such as ointments, creams, parenteral formulations, and the like, including intravaginally administered nonsolid formulations, the unit dose of the aryl-substituted N-alkyl indole is a concentration that will yield a unit dose within the above ranges. Thus, for example, when the desired unit dosage of the aryl-substituted N-alkyl indole is in the range of 10 mg to 150 mg, a concentration of the analog in the range of 0.25 wt. % to 30 wt. % is appropriate in a 500 mg to 4000 mg quantity of ointment, cream, or the like that is administered. As another example, when the desired unit dosage of the aryl-substituted N-alkyl indole is in the range of 20 mg to 50 mg, a concentration of the analog in the range of 0.5 wt. % to 10 wt. % is appropriate in a 500 mg to 4000 mg quantity of ointment, cream, or the like. As another example, when the desired unit dosage of the aryl-substituted N-alkyl indole is in the range of 20 mg to 50 mg, a concentration of the analog in the range of 1.0 wt. % to 5 wt. % is appropriate in a 1000 mg to 2000 mg quantity of ointment, cream, or the like.

The invention thus provides, in one embodiment, a pharmaceutical formulation for administration of an aryl-substituted N-alkyl indole of the invention to a subject, wherein the pharmaceutical formulation comprises a therapeutically effective amount of the aryl-substituted N-alkyl indole and at least one pharmaceutically acceptable excipient. In a related embodiment, the pharmaceutical formulation is a unit dosage form and comprises 5 mg to 500 mg of the aryl-substituted N-alkyl indole.

IV. Indications and Methods of Use

The aryl-substituted N-alkyl indoles of the invention exhibit affinity for at least one pharmacological receptor, i.e., a specialized target molecule within or on a cell that binds to a pharmacologically active agent and mediates its effect, wherein the receptors to which the aryl-substituted N-alkyl indoles of the invention exhibit affinity include the cannabinoid receptors CB1 and CB2 receptor; orphan G-protein coupled receptors (GPCRs) such as GPR55, GPR18, and GPR119; transient receptor potential (TRP) channels such as $TRPV_1$, $TRPA_1$, and TRPM8; serotonin receptors such as 5-HT1A, 5-HT2A, and 5-HT6; peroxisome proliferator-activated receptors (PPARs) such as PPAR-α and PPAR-γ; and additional CNS- and inflammation-related receptors such as sigma-1, adenosine A2A, and opioid receptors.

Accordingly, in one method, an aryl-substituted N-alkyl indole of the invention has utility in a method for binding to a pharmacological receptor. In one embodiment of the method, an aryl-substituted N-alkyl indole of the invention has utility in a method for binding to a cannabinoid receptor. In a related embodiment, an aryl-substituted N-alkyl indole of the invention is used to treat a disease, disorder or other adverse condition in a subject, wherein the disease, disorder or other adverse condition is one that is responsive to administration of a therapeutically effective amount of a compound that acts as a cannabinoid receptor binding ligand. By "responsive" is meant that administration of the aryl-substituted N-alkyl indole is effective as a disease-modifying therapy (DMT), i.e., a therapy that delays, slows, or reverses the progression of a disease.

An aryl-substituted N-alkyl indole of the invention typically exhibits a different level of activity at the CB1 receptor relative to the CB2 receptor (see, e.g., Example 11), i.e., exhibits greater selectivity at one of the two receptors. In some embodiments, an aryl-substituted N-alkyl indole of the invention exhibits moderate agonist activity at the $CB_1$ and/or $CB_2$ receptors. In some embodiments, an aryl-substituted N-alkyl indole of the invention is a biased $CB_1$ and/or $CB_2$ receptor agonist, selectively activating G protein signaling pathways relative to β-arrestin signaling pathways. In some embodiments, an aryl-substituted N-alkyl indole of the invention is a biased agonist of both the $CB_1$ and $CB_2$ receptors with minimal, if any, β-arrestin involvement. As such, unwanted side effects, particularly intoxicating effects, are avoided.

An aryl-substituted N-alkyl indole as provided herein may also exhibit a different type of activity, i.e., a different type of binding, at the CB1 receptor relative to the CB2 receptor, e.g., the aryl-substituted N-alkyl indole may act as an agonist, partial agonist, antagonist, inverse agonist, indirect agonist, or the like, at one but not both of the CB1 and CB2 receptors. See Example 14. For instance, compound (3) is a G-protein-biased partial agonist at the CB1 receptor and an inverse agonist at the CB2 receptor. An aryl-substituted N-alkyl indole herein may, therefore, be used in a method for selectively modulating a cannabinoid receptor, i.e., to enhance or reduce the activity of that receptor.

The aryl-substituted N-alkyl indole is generally administered to a subject within the context of an ongoing dosage regimen, although occasional, as-needed administration is also contemplated. The aryl-substituted N-alkyl indole is generally, although not necessarily, administered to the subject in a pharmaceutical formulation or dosage form, preferably in a unit dosage form.

As noted above, then, the compounds of the invention are useful in a method for treating a disease, disorder, or other adverse condition that is responsive to the administration of a compound that acts as a cannabinoid receptor binding ligand or other receptor binding ligand as alluded to above. Such diseases, disorders, and other adverse conditions encompass therapeutic indications including, without limitation, treatment of: pain; health conditions specific to women, such as endometriosis, dysmenorrhea, premenstrual syndrome, and uterine fibroid pain; alcoholism; anxiety; autism spectrum disorder; autoimmune disorders such as inflammatory bowel disease (IBD) (e.g., Crohn's disease, ileitis, ulcerative colitis), celiac disease, systemic lupus erythematosus, Addison's disease, Graves' disease, Hashimoto thyroiditis, myasthenia gravis, psoriasis, Sjögren's disease, pernicious anemia, vasculitis, autoimmune hepatitis, and type 1 diabetes; burns, including first-degree, second-degree, and third-degree burns, including thermal burns, radiation burns, chemical burns, and electrical burns; cancer, particularly cancers that tend to respond poorly to systemic chemotherapy, such as sarcomas, particularly osteosarcomas, brain cancers, and prostate cancers; cardiac disorders such as congestive heart failure, myocardial infarction, cardiomyopathy, and peripheral artery disease; cognitive pain and mild cognitive impairment; non-neurodegenerative dementia such as vascular dementia; demyelinating disorders such as multiple sclerosis, chronic inflammatory demyelinating polyneuropathy (CIDP), and Guillain-Barre Syndrome; dental disorders, primarily those associated with pain, inflammation, infection, and/or physical trauma, e.g., gingivitis and periodontitis; type 2 diabetes and glucose regulation; drug withdrawal, particularly opioid withdrawal (for instance, treatment of an individual who has stopped opioid use or is in the process of reducing the regular dosage of an opioid); fibroses, including kidney fibrosis, liver fibrosis, lung fibrosis, and systemic fibrosis; hypersensitivity-related maladies, particularly adverse skin reactions such as psoriasis, contact dermatitis, eczema, infectious skin ulcers, and cellulitis; immunodeficiency, including, but not limited to, primary immunodeficiency; inflammation, including inflammation-related arthritic disorders and inflammatory gastrointestinal disorders; ischemia, including cerebral ischemia, mesenteric ischemia, and kidney ischemia; infertility or limited fertility; liver diseases such as fatty liver disease, cirrhosis, and hepatitis; Metabolic Syndrome (Syndrome X) and any one of the conditions associated therewith; migraines and other types of headaches; nausea, including motion sickness; neurological and neurodegenerative disorders, including Alzheimer's disease, Parkinson's disease, Huntington's Disease, multiple sclerosis, amyotrophic lateral sclerosis, fronto-temporal dementia with Parkinson's features, progressive supranuclear palsies, essential dyskinesias, tardive dyskinesia, transverse myelitis, neurodegenerative cerebellar ataxia, aphasia, Bell's Palsy, Creutzfeldt-Jakob Disease, encephalitis, Amyotrophic Lateral Sclerosis (ALS), muscular dystrophy, and Meniere's Disease; obesity and overweight, as well as conditions caused by or associated with excess weight or obesity; osteoarthritis, osteoporosis, osteopenia, and regulation of bone mass; pelvic pain in both men and women; psychiatric disorders such as attention deficit hyperactivity disorder (ADHD), bipolar disorder, depression, obsessive compulsive disorder (OCD), post-traumatic stress disorder (PTSD), psychosis, and schizophrenia; respiratory disorders such as asthma, chronic obstructive pulmonary disease, bronchitis, and pneumonia; seizure disorders such as epilepsy; skin disorders such as acne and eczema; sleep disorders including apnea, insomnia, restless leg syndrome, and REM sleep dysfunction; and stress.

Treatment of pain is of particular interest, regardless of pain origin, duration, or severity. In one embodiment, then, an aryl-substituted N-alkyl indole of the invention is administered to a subject to treat pain, where the pain may be moderate or severe, acute or chronic, and may be, by way of example, post-surgical pain (such as pain associated with bunion surgery, dental surgery, or major surgery), pain incident to an injury, chemotherapy induced pain, pain associated with interstitial cystitis (bladder pain syndrome) and urinary tract infections, back pain of various types and origins, vascular-type pain such as that associated with migraines, and the like. An aryl-substituted N-alkyl indole of the invention is useful in a method to treat neuropathic pain, i.e., pain arising from nerve damage, such as central pain syndrome, complex regional pain syndrome, peripheral neuropathic pain (e.g., diabetic peripheral neuropathic pain), shingles and postherpetic neuralgia. The present compounds are also useful in a method for treating nociceptive pain, including somatic nociceptive pain, i.e., pain due to stimulation of peripheral nociceptors capable of responding to stimuli such as mechanical (pressure), thermal, chemical, and other stimulation; examples of nociceptive pain include pain associated with burn, fractures, incisions, wounds, cellulitis, shingles, arthritis, and gout. Nociceptive pain treatable with an aryl-substituted N-alkyl indole as provided herein also includes visceral pain, i.e., pain originating from viscera, muscles and bone, such as pain arising from tumor invasion, internal obstructions (e.g., of the bowel, ureter, or bile duct), colic, angina, and pancreatitis. Finally, an aryl-substituted N-alkyl indole as provided herein is useful to treat mixed pain, i.e., pain with both nociceptive and neuropathic symptoms. Examples of the foregoing include, without limitation, cancer pain, osteoarthritis pain, persistent postsurgical pain, and myofascial pain syndrome such as fibromyalgia.

In another embodiment, the invention provides a method for treating women's health conditions, such as endometriosis, primary and secondary dysmenorrhea, premenstrual syndrome, uterine fibroid pain and symptoms thereof, adenomyosis, polycystic ovary syndrome (PCOS), and menopausal symptoms, including a decrease in fertility. Evaluation of representative aryl-substituted N-alkyl indole (3) in the treatment of endometriosis pain is described in the examples herein. As with other methods of treatment herein, the aryl-substituted N-alkyl indole can be administered to the subject via any suitable mode of administration. However, it will be appreciated that for at least some of the aforementioned indications, vaginal administration of the active agent using a suppository is preferred.

In a further embodiment, the invention provides a method for treating a subject suffering from stress and/or anxiety, including chronic anxiety; anxiety associated with a specific anxiety disorder such as obsessive compulsive disorder, seasonal affective disorder, panic disorder, social anxiety disorder, and separation anxiety disorder; chronic or occasional difficulty sleeping; event-centric nervousness; generalized anxiety; post-traumatic stress disorder; and mild to moderate phobias.

In another embodiment, the invention provides a method for treating inflammation, i.e., for treating a condition, disease or disorder caused by or otherwise associated with inflammatory processes. In this embodiment, the method involves administration of an aryl-substituted N-alkyl indole as described herein to a subject afflicted with an inflammatory condition, disease, or disorder. Unabated inflammation plays a role in many disease pathologies, including, but not limited to, inflammation-related arthritic disorders such as rheumatoid arthritis, osteoarthritis, spondyloarthropathies (e.g., psoriatic arthritis) and myopathies, as well as inflammation-related myopathies that are not technically classified as arthritis, but involve similar symptoms, e.g., inflammation of tendons or ligaments ("soft tissue rheumatism") such as frozen shoulder, tennis elbow, carpal tunnel syndrome, plantar fasciitis, and Achilles tendonitis. This embodiment extends to a method for treating chronic gastrointestinal inflammation such as inflammatory bowel disease, or "IBD," which refers to any of a variety of diseases characterized by inflammation of all or part of the intestines. Examples of inflammatory bowel disease include, but are not limited to, Crohn's disease, Barrett's syndrome, ileitis, irritable bowel syndrome, irritable colon syndrome, ulcerative colitis, pseudomembranous colitis, hemorrhagic colitis, hemolytic-uremic syndrome colitis, collagenous colitis, ischemic colitis, radiation colitis, drug and chemically induced colitis, diversion colitis, colitis in conditions such as chronic granulomatous disease, celiac disease, celiac sprue, gastritis, and enterocolitis. As a subject may be experiencing pain and inflammation as co-occurring disorders or as related to co-occurring disorders, or pain and inflammation may both be caused by or associated with the same underlying pathology, the methods of the invention extend to the treatment of both pain and inflammation occurring simultaneously in the same individual (as may be the case, for instance, following surgery or injury, or associated with certain disorders, e.g., arthritis).

A further embodiment of the invention pertains to weight management, including the promotion of weight loss in a subject by reducing appetite and/or effecting metabolic changes. The method includes administering an effective amount of an aryl-substituted N-alkyl indole of the invention to a subject who could benefit from losing weight, e.g., a subject who is overweight or obese. Also provided are methods for treating conditions caused by or associated with excess weight or obesity, where the conditions include type 2 diabetes; insulin resistance; impaired glucose tolerance; gallbladder disease; dyslipidemia, e.g., high cholesterol, elevated triglyceride levels, and/or elevated levels of low-density lipoprotein (LDL); gout; hypertension; and metabolic disorders such as Metabolic Syndrome (Syndrome X, including insulin-resistant Syndrome X), individual conditions associated with metabolic syndrome, and hypoalphalipoproteinemia.

In any of the foregoing methods, the aryl-substituted N-alkyl indole can be administered to the subject as a monotherapy, e.g., in lieu of opioid administration, such as in transitioning a patient from an opioid dosing regimen to a dosing regimen comprising regular or as-needed administration of a therapeutically effective amount of an aryl-substituted N-alkyl indole of the invention (in which case the opioid dosage is gradually reduced prior to beginning administration of a compound as provided herein). Alternatively, an aryl-substituted N-alkyl indole of the invention may be co-administered with at least one additional active agent in a combination therapy, in which case the aryl-substituted N-alkyl indole and the additional active agent(s) may be administered simultaneously or sequentially, and, if administered simultaneously, may be administered in a single dosage form or in separate dosage forms. Any additional active agent that is co-administered with the aryl-substituted N-alkyl indole will generally, although not necessarily, be selected for its utility in treating the same indication as the aryl-substituted N-alkyl indole. In a related embodiment, a method is provided for transitioning a pain patient from an opioid dosing regimen to a dosing regimen comprising regular or as-needed administration of a therapeutically effective amount of an aryl-substituted N-alkyl indole of the invention.

In the present method for treating pain, for example, suitable secondary active agents are also, preferably, analgesic agents, and may be, by way of example, a nonsteroidal anti-inflammatory agent (NSAID) (e.g., ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, apazone, diclofenac, difenpiramide, diflunisal, etodolac, indomethacin, ketorolac, meclofenamate, nabumetone, phenylbutazone, piroxicam, sulindac, tolmetin, etc.), a steroidal anti-inflammatory agent (e.g., hydrocortisone, hydrocortisone-21-monoesters such as hydrocortisone-21-acetate, hydrocortisone-21 butyrate, hydrocortisone-21-propionate, hydrocortisone-21-valerate); hydrocortisone-17,21-diesters such as hydrocortisone-17,21-diacetate, hydrocortisone-17-acetate-21-butyrate, hydrocortisone-17,21-dibutyrate); alclometasone, dexamethasone, flumethasone, prednisolone, methylprednisolone, etc.), a non-opioid analgesic agent (e.g., acetaminophen, apazone, etodolac, difenpiramide, indomethacin, meclofenamate, mefenamic acid, oxaprozin, phenylbutazone, piroxicam, tolmetin, etc.), an opioid analgesic agent (e.g., alfentanil, buprenorphine, butorphanol, codeine, dihydrocodeine, fentanyl, hydrocodone, hydromorphone, levorphanol, meperidine, methadone, morphine, nalbuphine, oxycodone, oxymorphone, pentazocine, propoxyphene, sufentanil, tramadol, etc.), or the like.

Co-administration of an aryl-substituted N-alkyl indole as provided herein with an opioid analgesic agent is of particular interest insofar as a combination formulation, or separate co-administration, will reduce the therapeutic dosage of the opioid required and eliminate or at least minimize many of the undesirable side effects associated with opioid use, such as sedation, dizziness, tolerance, physical dependence, and the like. See Nielsen et al. (2017), "Opioid-Sparing Effect of Cannabinoids" A Systematic Review and Meta-Analysis," Neuropsychopharmacology 42(9): 1752-1765, which indicates that the median effective dose (ED50) of morphine administered in combination with A9-THC is 3.6 times lower than the ED50 of morphine alone. Co-administration of an aryl-substituted N-alkyl indole with an opioid analgesic can also exhibit synergistic activity, with increased analgesic efficacy and/or reduced side effects seen relative to either drug administered as a monotherapy. Accordingly, in some embodiments, the invention provides a method for reducing the therapeutic dosage of an opioid administered to a subject to treat pain, and/or eliminating or at least minimizing side effects of opioid administration, wherein the method involves co-administering an aryl-substituted N-alkyl indole of the invention to the subject in combination with the opioid, either simultaneously or sequentially.

Secondary active agents for co-administration with the aryl-substituted N-alkyl indole in the treatment of inflammatory conditions include, by way of example, non-steroidal anti-inflammatory agents (NSAIDs), including those identified above as suitable in the treatment of pain; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; oxicams such as meloxicam and piroxicam; nabumetone; phenylbutazone; piroxicam; salicylates such as salsalate and acetylsalicylic acid; sulfasalazine; sulindac; tolmetin; and COX-2 inhibitors such as celecoxib, rofecoxib, and valdecoxib. The secondary active agent may also be selected from steroidal anti-inflammatory agents, including corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, and methylprednisolone.

Secondary active agents for co-administration with the aryl-substituted N-alkyl indole in the method for managing weight loss and treating related conditions (overweight, obesity, type 2 diabetes, metabolic syndrome, and the like, as detailed above) include glucagon-like peptide 1 receptor agonists (GLP-1 RAs), which have become popular in the treatment of obesity and related conditions because they lower both hemoglobin A1C and weight while exhibiting a very low risk of hypoglycemia; some GLP-1 RAs also have documented cardiovascular benefits. Examples of GLP-1 RAs that can be beneficially administered in a combined dosage regimen with an aryl-substituted N-alkyl indole analog of the invention include exenatide, liraglutide, albiglutide, dulaglutide, lixisenatide, semaglutide, and tirzepatide. In one embodiment, the method involves administration of an aryl-substituted N-alkyl indole of the invention at the beginning of an ongoing dosage regimen, e.g., during the first week, two weeks, three weeks, two months, three months, six months, with addition of the selected GLP-1 RA at a later point in the dosage regimen, e.g., after the first week, after the first two weeks, three weeks, two months, three months, six months, etc. The unit dosage and daily dosage of the aryl-substituted N-alkyl indole are as described earlier herein, and the unit dosage and daily dosage of the GLP-1 RA are amounts within the approved dosage range for the selected GLP-1 RA. The combined dosing is continued until the desired end result is achieved, e.g., a significant reduction in weight, lowered hemoglobin A1C, lowered blood pressure, or the like.

Secondary active agents to administer with an aryl-substituted N-alkyl indole of the invention for the treatment of endometriosis include, without limitation, progesterone or another naturally occurring, synthetic, or semi-synthetic progestogen (the latter two generally referred to as "progestins"), such as desogestrel, ethisterone, etonorgestrel, hydroxyprogesterone (or esters thereof), medroxyprogesterone (or esters thereof), megestrol, and the like; hormonal contraceptives in which a progestogen is combined with an estrogenic compound such as estradiol (i.e., 17β-estradiol) or an ester thereof, estrone, ethinylestradiol, etc., as may be administered in the form of a birth control pill, a transdermal patches, an IUD, or the like; and GnRH antagonists (e.g., elagolix and linzagolix) and GnRH agonists (e.g., triptorelin, leuprorelin, buserelin, etc.). Examples of other secondary active agents that may be beneficial to co-administer with an aryl-substituted N-alkyl indole of the invention for the treatment of endometriosis include aromatase inhibitors (e.g., letrozole and anastrozole); NSAIDs such as those identified above as secondary agents to co-administer with an aryl-substituted N-alkyl indole in the treatment of pain and inflammatory conditions; and analgesic agents, including both non-opiate analgesic agents and opiate analgesic agents such as those mentioned above for the treatment of pain.

Also of interest are combinations comprising at least one aryl-substituted N-alkyl indole of the invention and a second beneficial agent in the form of a nutritional supplement, where the nutritional supplement, in one embodiment, is selected from vitamins, vitamin metabolites, vitamin derivatives, provitamins, and vitamin cofactors, e.g., vitamin $A_1$ (all-trans-retinol), vitamin A aldehyde (retinal), retinoic acid, provitamin A carotenoids (alpha-carotene, beta-carotene, gamma-carotene), xanthophyll beta-cryptoxanthin), vitamin $B_1$ (thiamine), thiamine monophosphate, thiamine pyrophosphate, riboflavin (vitamin $B_2$), flavin mononucleotide (FMN), flavin adenine dinucleotide (FAD), niacin (vitamin $B_3$), niacinamide, nicotinamide riboside, nicotinamide adenine dinucleotide phosphate (NADP), pantothenic acid (vitamin $B_5$), pantothenol, pantethine, pyridoxine (vitamin B), pyridoxal, pyridoxal phosphate, pyridoxamine, biotin (vitamin $B_7$), folate (vitamin $B_9$), folic acid, tetrahydrofolic acid, cobalamin (vitamin $B_{12}$), methylcobalamin, hydroxocobalamin (vitamin $B_{123}$), adenosylcobalamin, cyanocobalamin, ascorbic acid (vitamin C), calciferols (vitamin D) including vitamin $D_1$ (a 1:1 mixture of ergocalciferol and lumisterol), ergocalciferol (vitamin $D_2$), cholecalciferol (vitamin $D_3$), vitamin E (alpha-tocopherol, beta-tocopherol, gamma-tocopherol, delta-tocopherol, tocopheryl acetate, alpha-tocotrienol, beta-tocotrienol, gamma-tocotrienol, and delta-tocotrienol), vitamin $K_1$ (phylloquinone), vitamin $K_2$ (menaquinone), choline, carnitine, coenzyme A, and coenzyme Q10.

In another embodiment, the nutritional supplement is a mineral, i.e., an inorganic substance that is required in the human diet, including, without limitation, calcium, magnesium, iron, zinc, selenium, copper, manganese, chromium, molybdenum, etc.

In still another embodiment, the nutritional supplement may be selected from amino acids, peptides, proteins, hormones, probiotics, fatty acids and other lipids, anti-oxidants, essential oils, fiber supplements, herbal supplements, botanicals, plant extracts, and the like, with specific such supplements including, for example, terpenoids, curcumin, resveratrol, lignans, carnosine, chondroitin sulfate, creatine, dehydroepiandrosterone, 5-hydroxytryptophan, collagen, indole-3-carbinol, methylsulfonylmethane, phospholipids, phytosterols, essential fatty acids (e.g., omega-3 fatty acids), green tea polyphenols, quercetin and other flavonoids, S-adenosylmethionine, and theobromine, among others. Further examples of suitable nutrients include those listed in Handbook of Nutraceuticals and Functional Foods, Robert E. C. Wildman, Ed., CRC Press (2001).

It is to be understood that while the invention has been described in conjunction with a number of specific embodiments, the foregoing description as well as the examples that follow are intended to illustrate and not limit the scope of the invention.

All patents, patent publications, literature references, and other materials cited herein are incorporated by reference in their entireties.

Example 1

Synthesis of Methyl 3-(2-(isoquinolin-1-yl) ethyl)-1-methyl-2-morpholino-1H-indole-6-carboxylate (1)

Scheme (1)

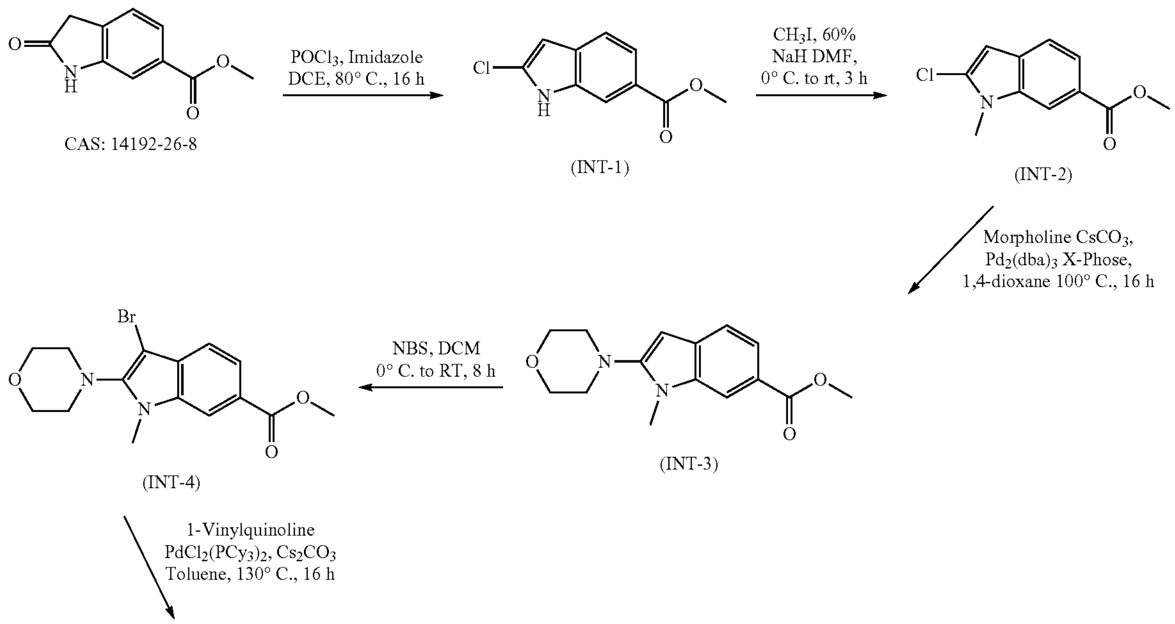

-continued

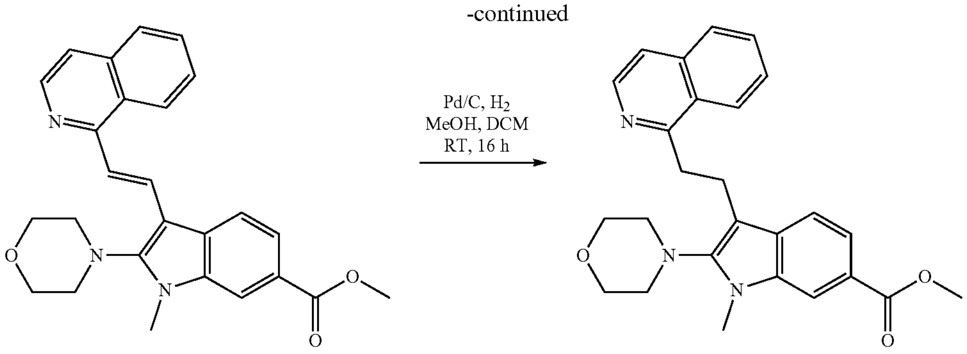

(INT-5)

(1)

Aryl-Substituted N-Alkyl Indole (1) (methyl 3-(2-(isoquinolin-1-yl) ethyl)-1-methyl-2-morpholino-1H-indole-6-carboxylate) was synthesized according to Scheme 1, as follows:

Step 1: Synthesis of methyl 2-chloro-1H-indole-6-carboxylate (INT-1): To a stirred solution of methyl 2-oxoindoline-6-carboxylate (CAS: 14192-26-8) (25.0 g, 1.0 eq.) in DCE (625.0 mL, 25.0 vol.) was added $POCl_3$ (150.0 mL, 6.0 vol.) at room temperature followed by addition of Imidazole (35.6 g, 4.0 eq.) at the same temperature. The reaction mixture was further heated and stirred at 80° C. for 16 hours, with monitoring by TLC analysis (using 5:5 EtAOc: Hexane). After completion of the reaction, the reaction mixture was quenched with sat. $Na_2CO_3$ solution (1500.0 mL) and extracted with DCM (4×500 mL). The organic layers were combined, dried over $Na_2SO_4$, and concentrated under reduced pressure to afford crude material. The crude material was purified by normal phase column chromatography using 20% EtOAc in hexane to obtain the pure title intermediate methyl 2-chloro-1H-indole-6-carboxylate (INT-1) (17.0 g, 62% yield) as an off-white solid.

Analysis:

LCMS: 99.0%, RT: 2.168 min (@220.0 nm), MS: ES+ 210.2 [M+1].

$^1$H NMR (400 MHz, DMSO-d6): δ 12.33 (s, 1H), 7.94 (s, 1H), 7.65 (dd, J=1.2, 1.2 Hz, 1H), 7.67 (d, J=8.0 Hz, 1H), 6.58 (s, 1H), 3.83 (s, 3H).

Step 2: Synthesis of methyl 2-chloro-1-methyl-1H-indole-6-carboxylate (INT-2)

To a stirred solution of methyl 2-chloro-1H-indole-6-carboxylate (INT-1) (17.0 g, 1.0 eq.) in DMF (170.0 mL, 10 vol.) was added 60% NaH (9.7 g, 3.0 eq.) portion wise at 0° C. and the reaction mixture was allowed to stir at the same temperature for 30 min. After 30 min, Mel (7.8 mL, 1.5 eq.) was added dropwise to the reaction mixture at the same temperature. The reaction mixture was further warmed to rt and stirred at the same temperature for 3 hours. The reaction mixture was monitored by TLC analysis (using 3:7 EtOAc: hexane). After completion of the reaction, the reaction mixture was quenched by cold water (100 mL) and extracted with EtOAc (3×100 mL). The organic layers were combined, dried over $Na_2SO_4$, and concentrated under reduced pressure to obtain the title intermediate methyl 2-chloro-1-methyl-1H-indole-6-carboxylate (INT-2) (16.0 g, 88% yield) as off white solid.

Analysis:

LCMS: 94.4%, RT: 2.393 min (@254.0 nm), MS: ES+ 224.1 [M+1].

$^1$H NMR (400 MHz, DMSO-d6): δ8.11 (s, 1H), 7.70 (dd, J=1.6, J=1.6 Hz, 1H), 7.59-7.61 (m, 1H), 6.71 (d, J=0.8 Hz, 1H), 3.87 (s, 3H), 3.82 (s, 3H).

Step 3: Synthesis of methyl 1-methyl-2-morpholino-1H-indole-6-carboxylate (INT-3)

To a stirred solution of methyl 2-chloro-1-methyl-1H-indole-6-carboxylate (INT-2) (16.0 g, 1.0 eq.) and morpholine (18.7 g, 3.0 eq.) in 1,4-dioxane (160.0 mL, 10.0 vol.) was added cesium carbonate (70.17 g, 3.0 eq.) at room temperature. The reaction mixture was purged with $N_2$ gas for 30 min and $Pd_2(db_2)_3$ (13.1 g, 0.2 eq.) was added to the reaction mixture followed by X-Phose (6.8 g, 0.2 eq.) at same temperature. The reaction mixture was further heated to 100° C. and allowed to stir at the same temperature for 16 hours. The reaction mixture was monitored by TLC analysis (using 2:8 EtOAc:hexane). After completion of the reaction, the reaction mixture was diluted with water (200.0 mL) and extracted with ethyl acetate (3×200.0 mL). The organic layers were combined, dried over $Na_2SO_4$, and concentrated under reduced pressure to afford crude material. The crude material was purified by normal phase column chromatography using 50% EtOAc in hexane to obtain the pure title intermediate methyl 1-methyl-2-morpholino-1H-indole-6-carboxylate (INT-3) (10.0 g, 50.9% yield) as brown solid.

Analysis:

LCMS: 70.4%, RT: 2.185 min (@220.0 nm), MS: ES+ 275.2 [M+1].

$^1$H NMR (400 MHz, DMSO-d6): δ 7.94 (m, 1H), 7.62 (dd, J=1.2, J=1.2 Hz, 1H), 7.46 (d, J=8.4 Hz, 1H), 6.00 (s, 1H), 3.84 (s, 3H), 3.79 (t, J=4.4 Hz, 4H), 3.66 (s, 3H), 3.01 (t, J=4.8 Hz, 4H).

Step 4: Synthesis of methyl 3-bromo-1-methyl-2-morpholino-1H-indole-6-carboxylate (INT-4)

To a stirred solution of methyl 1-methyl-2-morpholino-1H-indole-6-carboxylate (INT-3) (10.0 g, 1.0 eq.) in DCM (100.0 mL, 10.0 vol.) was added N-bromosuccinimide (6.98 g, 1.1 eq.) portion wise at 0° C. The reaction mixture was allowed to warm to room temperature and stirred at the same temperature for 8 hours. The reaction mixture was monitored by TLC analysis (using 2:8 EtOAc in hexane). After completion of the reaction, the reaction mixture was diluted with water (150.0 mL) and extracted with DCM (4×100.0 mL). The organic layers were combined, dried over $Na_2SO_4$, and concentrated under reduced pressure to afford crude material. The crude material was purified by normal phase column chromatography using 50% EtOAc in hexane to obtain the pure title intermediate methyl 3-bromo-1-methyl-2-morpholino-1H-indole-6-carboxylate (INT-4) (8.0 g, 62% yield) as brown solid.

Analysis:

LCMS: 92.5%, RT: 2.476 min (@224.0 nm), MS: ES+ 353.1 [M], 355.0 [M+2].

$^1$H NMR (400 MHz, DMSO-d6): δ 8.03 (d, J=0.8 Hz, 1H), 7.74 (dd, J=1.2, J=1.6 Hz, 1H), 7.41 (d, J=8.4, 1H), 3.87 (s, 3H), 3.77 (t, J=4.4 Hz, 4H), 3.72 (s, 3H), 3.28 (t, J=4.4 Hz, 4H).

Step 5: Synthesis of methyl (E)-3-(2-(isoquinolin-1-yl) vinyl)-1-methyl-2-morpholino-1H-indole-6-carboxylate (INT-5)

(a) Synthesis of 1-vinylisoquinoline: To a stirred solution of 1-chloroisoquinoline (CAS: 19493-44-8) (20 g, 1.0 eq.) and CAS: 13682-77-4 (19.7 g, 1.2 eq.) in IPA (100 mL, 10 vol.) was added TEA (8 mL, 1.0 eq.) at room temperature. The reaction mixture was purged with $N_2$ gas for 30 min. and $PdCl_2$(dppf). DCM (1.0 g, 0.02 eq.) was added to the reaction mixture at same temperature. The reaction mixture was further heated and stirred at 80° C. for 16 hours, with monitoring carried out by TLC analysis (using 2:8 EtOAc: hexane). After completion of the reaction, the reaction mixture was concentrated under reduced pressure to afford crude material. The crude material was purified by normal phase column chromatography using 50% EtOAc in hexane to give 1-vinylisoquinoline (8.0 g, 42% yield) as yellow solid.

Analysis:

LCMS: 88.27%, RT: 1.070 min. (@220.0 nm), MS: ES+ 156.0 [M+1].

$^1$H NMR (400 MHz, DMSO-d6): δ 8.54 (d, J=5.6 Hz, 1H), 8.27 (d, J=8.4 Hz, 1H), 7.83 (d, J=8.4 Hz, 1H), 7.58-7.70 (m, 4H), 6.52-6.56 (m, 1H), 5.72-5.75 (m, 1H).

(b) Synthesis of (INT-5) from 1-vinylisoquinoline and (INT-4): To a stirred solution of methyl 3-bromo-1-methyl-2-morpholino-1H-indole-6-carboxylate (INT-4) (8.0 g, 1.0 eq.) and 1-vinylisoquinoline (3.86 g, 1.1 eq.) in toluene (80.0 mL, 10.0 vol.) was added cesium carbonate (22.1 g, 3.0 eq.) at room temperature. The reaction mixture was further purged with $N_2$ gas for 30 min and $Pd_2(PCy)_3$ (0.34 g, 0.02 eq.) was added to the reaction mixture at room temperature. The reaction mixture was further heated and allowed to stir at 120° C. for 16 hour, with monitoring carried out using TLC analysis (using 5:5 EtOAc:hexane). After completion of the reaction, the reaction mixture was quenched with water (100 mL) and extracted with ethyl acetate (3×100 mL). The organic layers were combined, dried over $Na_2SO_4$, and concentrated under reduced pressure to afford crude material. The crude material was purified by normal phase column chromatography using 50% EtOAc in hexane to obtain pure title intermediate methyl (E)-3-(2-(isoquinolin-1-yl) vinyl)-1-methyl-2-morpholino-1H-indole-6-carboxylate (INT-5) (5.5 g, 56.8% yield) as yellow solid.

Analysis:

LCMS: 75.0%, RT: 1.541 min (@220.0 nm), MS: ES+ 428.2 [M+1].

Step 6: Synthesis of methyl 3-(2-(isoquinolin-1-yl) ethyl)-1-methyl-2-morpholino-1H-indole-6-carboxylate (1)

To a stirred solution of methyl (E)-3-(2-(isoquinolin-1-yl) vinyl)-1-methyl-2-morpholino-1H-indole-6-carboxylate (INT-5) (5.5 g, 1.0 eq.) in MeOH:DCM (1:1, 20.0 vol.) was added 10% palladium on carbon (5.5 g, w/w) at room temperature. The reaction mixture further purged with hydrogen gas for 16 hours. The reaction mixture was monitored by TLC analysis (using 5:5, EtOAc in hexane). After completion of the reaction, the reaction mixture was diluted with MeOH (50.0 mL) and filtered through a celite pad, and the filtrate was concentrated under reduce pressure to obtain the pure title intermediate methyl 3-(2-(isoquinolin-1-yl) ethyl)-1-methyl-2-morpholino-1H-indole-6-carboxylate (1) (5.0 g, 90.9% yield) as a brown solid.

Analysis:

LCMS: 6.10%, RT: 1.823 min (220.0 nm), MS: ES+ 430.3 [M+1].

Example 2

Synthesis of (3-(2-(Isoquinolin-1-yl) ethyl)-1-methyl-2-morpholino-1H-indole-6-yl) methanol (2)

Scheme (2)

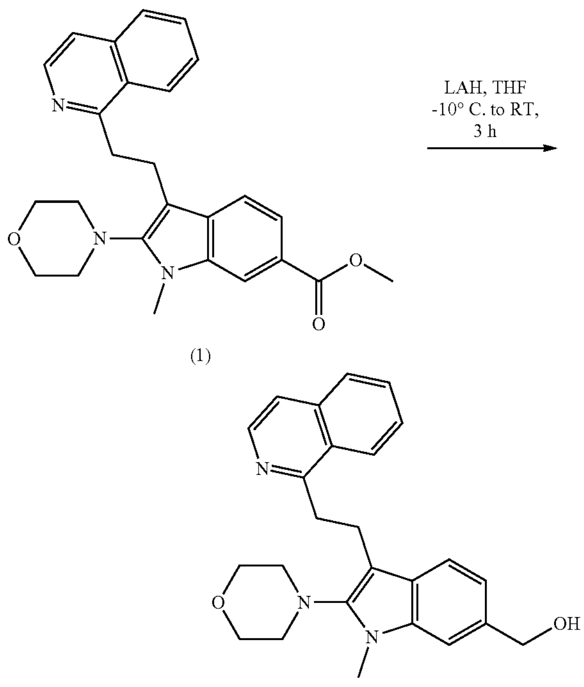

(1)

(2)

Aryl-Substituted N-Alkyl Indole (2) ((3-(2-(isoquinolin-1-yl) ethyl)-1-methyl-2-morpholino-1H-indole-6-yl) methanol) was synthesized according to the reaction of Scheme (2), as follows:

To a stirred solution of methyl 3-(2-(isoquinolin-1-yl) ethyl)-1-methyl-2-morpholino-1H-indole-6-carboxylate (1) (5.0 g, 1.0 eq.) in dry THF (50.0 mL, 10.0 vol.) was added LAH (17.4 mL, 1M in THF, 1.5 eq.) dropwise at −10° C. under $N_2$ atm. The reaction mixture was gradually warmed to room temperature and stirred at same temperature for 5 hours. The reaction mixture was monitored by TLC analysis (using 5:5 EtOAc:hexane). After completion of the reaction, the reaction mixture was quenched by $NH_4Cl$ sol. (150.0 mL) and extracted with ethyl acetate (3×150.0 mL). The organic layers were combined, dried over $Na_2SO_4$, and concentrated under reduced pressure to afford crude material. The crude material was purified by normal phase column chromatography using 35% EtOAc in hexane to obtain the pure title compound (3-(2-(isoquinolin-1-yl) ethyl)-1-methyl-2-morpholino-1H-indol-6-yl) methanol (2) (3.5 g, 74.9% yield) as brown solid.

Analysis:

LCMS: 96.41%, RT: 1.650 min (@285.0 nm), MS: ES+ 402.3 [M+1].

HPLC: 98.39%, RT: 4.058 min (@254.0 nm)

$^1$H NMR (400 MHz, DMSO-d6): δ 8.45 (d, J=5.6 Hz, 1H), 8.21 (d, J=8.8 Hz, 1H), 7.96 (d, J=8.4 Hz, 1H), 7.76 (t, J=7.2 Hz, 1H), 7.64-7.70 (m, 2H), 7.41 (d, J=8.0 Hz, 1H), 7.23 (s, 1H), 6.97 (d, J=8.4 Hz, 1H), 5.05 (t, J=5.6 Hz, 1H), 4.57 (d, J=5.6 Hz, 2H), 3.68 (t, J=4.4 Hz, 1H), 3.51-3.56 (m, 5H), 3.23-3.27 (m 2H), 3.05 (t, J=4.4 Hz, 1H).

Example 3

Synthesis of 2-(3-(2-(Isoquinolin-1-yl) ethyl)-1-methyl-2-morpholino-1H-indol-6-yl) acetonitrile (3)

Scheme (3)

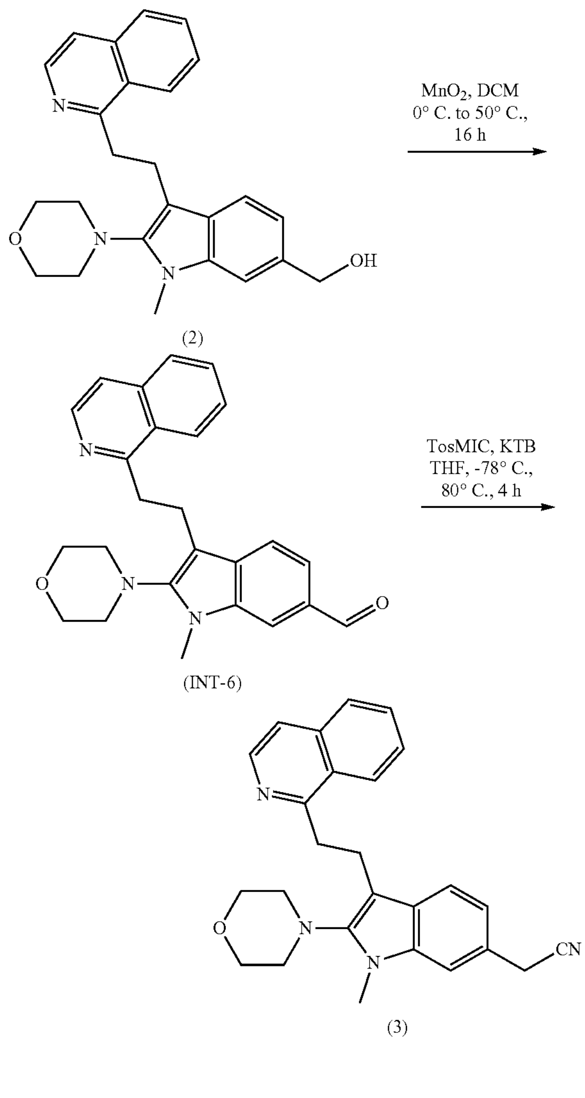

(2)

(INT-6)

(3)

Aryl-Substituted N-Alkyl Indole (3) ((3-(2-(isoquinolin-1-yl) ethyl)-1-methyl-2-morpholino-1H-indole-6-yl) acetonitrile) was synthesized according to the reaction of Scheme (3), as follows:

Step 1: Synthesis of 3-(2-(isoquinolin-1-yl) ethyl)-1-methyl-2-morpholino-1H-indole-6-carbaldehyde (INT-6)

To a stirred solution of (3-(2-(isoquinolin-1-yl) ethyl)-1-methyl-2-morpholino-1H-indol-6-yl) methanol (2) (3.5 g, 1.0 eq.) in DCM (35 mL, 10 vol.) was added $MnO_2$ (7.59 g, 10 eq.) portion wise at 0° C. The reaction mixture was stirred at the same temperature for 30 min and further heated to 50° C., then stirred at 50° C. for 16 hours. The reaction mixture was monitored by TLC analysis (using 5:5 EtOAc:hexane). After completion of the reaction, the reaction mixture was filtered through a celite pad and the collected filtrate was concentrated under reduced pressure to give 3-(2-(isoquinolin-1-yl) ethyl)-1-methyl-2-morpholino-1H-indole-6-carbaldehyde (INT-6) (2.5 g, 71.8% yield) as a light brown solid.

Analysis:

LCMS: 93.85%, RT: 1.790 min (@210.0 nm), MS: ES+ 400.3 [M+1].

1H NMR (400 MHz, DMSO-d6): δ 9.96 (s, 1H), 8.44 (d, J=6.0 Hz, 1H), 8.19 (d, J=8.4 Hz, 1H), 7.95 (d, J=8.4 Hz, 1H), 7.89 (s, 1H), 7.62-7.73 (m, 31H), 7.52-7.57 (m, 2H), 3.78 (bs, 4H), 3.67 (s, 3H), 3.53-3.57 (m, 2H), 3.32 (s, 2H), 3.11 (t, J=4.4 Hz, 4H).

Step 2: Synthesis of 2-(3-(2-(isoquinolin-1-yl) ethyl)-1-methyl-2-morpholino-1H-indol-6-yl) acetonitrile (3)

To a stirred solution of potassium t-butoxide (KTB) (1.75 g, 1.0 eq.) in dry THF (75.0 mL, 10 vol.) was added p-toluenesulfonylmethyl isocyanide (TosMIC) (1.22 g, 1 eq.) at −78° C. and the reaction mixture was stirred at the same temperature for 45 min. After 45 min, 3-(2-(isoquinolin-1-yl) ethyl)-1-methyl-2-morpholino-1H-indole-6-carbaldehyde (INT-6) (2.5 g, 1.0 eq.) was added to the reaction mixture at same temperature, the mixture was gradually warmed to room temperature and stirred at room temperature for 30 min. After 30 min, MeOH was added to the reaction mixture and the mixture was stirred at 80° C. for 30 min. The reaction mixture was monitored by TLC analysis (using 5:5, EtOAc:hexane). After completion, AcOH (0.03 mL, 0.5 vol.) was added to the reaction mixture, and the mixture was concentrated under reduced pressure to obtain the residue. The obtained residue was diluted with water (50.0 mL) and extracted with EtOAc (3×50.0 mL). The organic layers were combined, dried over $Na_2SO_4$, and concentrated under reduced pressure to afford crude material. The crude material was purified by normal phase column chromatography using 40% ethyl acetate in hexane to give 2-(3-(2-(isoquinolin-1-yl) ethyl)-1-methyl-2-morpholino-1H-indol-6-yl) acetonitrile (3) (1.1 g, 42.8% yield) as light pink solid.

Analysis:

LCMS: 100%, RT: 1.846 min (@235.0 nm), MS: ES+ 411.3 [M+1].

HPLC: 97.51%, RT: 4.899 min (@210.0 nm)

$^1$H NMR (400 MHz, DMSO-d6): δ 8.46 (d, J=5.6 Hz, 1H), 8.22 (d, J=8.4 Hz, 1H), 7.97 (d, J=8.0 Hz, 1H), 7.77 (t, J=7.2 Hz, 1H), 7.64-7.71 (m, 2H), 7.48 (d, J=8.0 Hz, 1H), 7.28 (s, 1H), 6.97-6.99 (m, 1H), 4.07 (s, 2H), 3.70 (t, J=4.8 Hz, 1H), 3.52-3.58 (m, 5H), 3.25-3.29 (m, 2H), 3.06 (t, J=4.0 Hz, 4H).

Example 4

Synthesis of 2-(3-(2-(Isoquinolin-1-yl) ethyl)-1-methyl-2-morpholino-1H-indol-6-yl) acetic acid (4)

Scheme (4)

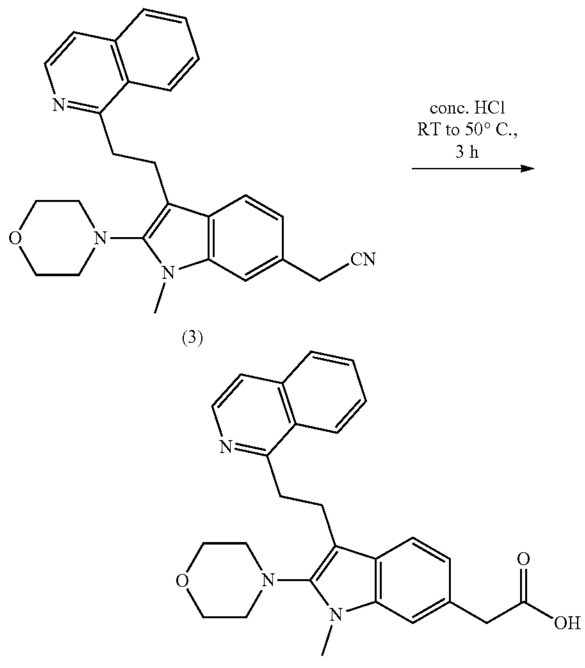

(3)

(4)

Aryl-Substituted N-Alkyl Indole (4) (2-(3-(2-(isoquinolin-1-yl) ethyl)-1-methyl-2-morpholino-1H-indole-6-yl) acetic acid) was synthesized according to the reaction of Scheme (4), as follows:

In a 25 ml RBF was taken 2-(3-(2-(isoquinolin-1-yl) ethyl)-1-methyl-2-morpholino-1H-indol-6-yl) acetonitrile (3) (0.8 g, 1.0 eq.) in conc. HCl (10 Vol.) at room temperature. The reaction mixture was gradually heated to 50° C. and stirred at the same temperature for 3 hours. The reaction mixture was monitored by TLC analysis (using 1:9 MeOH: DCM). After completion of the reaction, the reaction mixture was quenched with aq. $NaHCO_3$ sol. (25 mL) and extracted with ethyl acetate (2×50 mL). The organic layers were combined, dried over $Na_2SO_4$, and concentrated under reduced pressure to afford crude material. The crude material was purified by normal phase column chromatography using 0-5% MeOH in DCM to give 2-(3-(2-(isoquinolin-1-yl) ethyl)-1-methyl-2-morpholino-1H-indol-6-yl) acetic acid (4) (0.35 g, 41.8% yield) as light brown solid.

Analysis:

LCMS: 96.59%, RT: 1.677 min (@254.0 nm), MS: ES+ 430.3 [M+1].

HPLC: 94.53%, RT: 4.306 min (@210.0 nm)

$^1$H NMR (400 MHz, DMSO-d6): δ 12.21 (s, 1H), 8.46 (d, J=5.6 Hz, 1H), 8.23 (d, J=8.4 Hz, 1H), 7.97 (d, J=8.0 Hz, 1H), 7.77 (t, J=7.6 Hz, 1H), 7.66-7.71 (m, 2H), 7.43 (d, J=8.0 Hz, 1H), 7.18 (s, 1H), 6.92 (d, J=8.0 Hz, 1H), 3.69 (t, J=4.8 Hz, 1H), 3.61 (s, 2H), 3.52-3.59 (m, 5H), 3.24-3.28 (m, 2H), 3.06 (bs, 4H).

Example 5

Synthesis of 2-(3-(2-(Isoquinolin-1-yl) ethyl)-1-methyl-2-morpholino-1H-indol-6-yl)-1-(morpholin-4-yl) ethan-1-one (5)

Scheme (5)

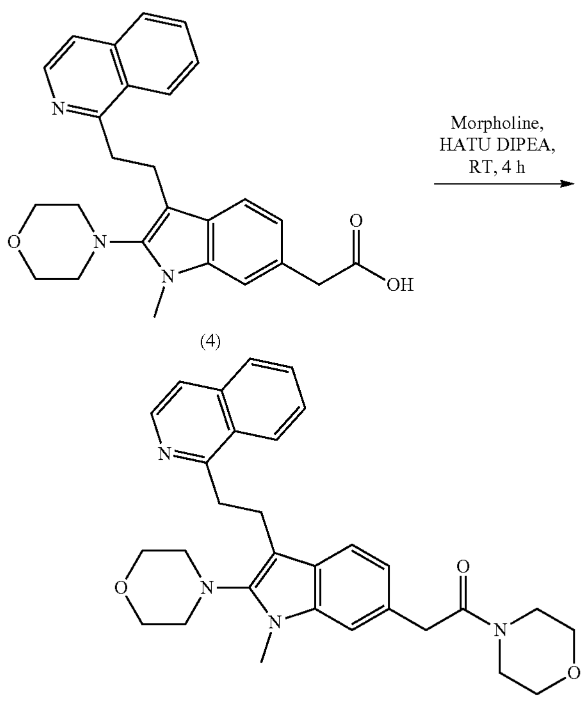

(4)

(5)

Aryl-Substituted N-Alkyl Indole (5) (2-(3-(2-(isoquinolin-1-yl) ethyl)-1-methyl-2-morpholino-1H-indole-6-yl)-1-(morpholin-4-yl) ethan-1-one) was synthesized according to the reaction of Scheme (5), as follows:

To a solution of 2-(3-(2-(isoquinolin-1-yl) ethyl)-1-methyl-2-morpholino-1H-indol-6-yl) acetic acid (4) (100 mg, 1.0 eq., 0.23 mmol) in dry DMF (2 mL) were added morpholine (0.02 mL, 1.0 eq., 0.23 mmol), 0-(7-azabenzotriazol-1-yl)-N,N,N',N'-tetramethyluronium hexafluorophosphate (HATU) (104 mg, 1.1 eq., 0.25 mmol), and DIPEA (0.12 mL, 3.0 eq., 0.69 mmol) at room temperature under nitrogen. The reaction mixture was stirred at room temperature for 4 hours and monitored by TLC (10% MeOH in DCM). Upon completion, the reaction was quenched with water (10 mL) and extracted with ethyl acetate (2×20 mL). The organic layers were combined, dried over $Na_2SO_4$, filtered, and concentrated under reduced pressure. The crude product was purified by flash column chromatography (0-5% MeOH in DCM) to afford (5) as a light brown solid in 65% yield.

Analysis:

LCMS: 100%, RT: 1.812 min (@220 nm), 1.855 min (@295 nm), MS: ES+ 499.4 [M+1]

Example 6
Synthesis of 2-(3-(2-(6-Acetamidoisoquinolin-1-yl)ethyl)-1-methyl-2-morpholino-1H-indol-6-yl)acetonitrile (19)
Scheme (6)
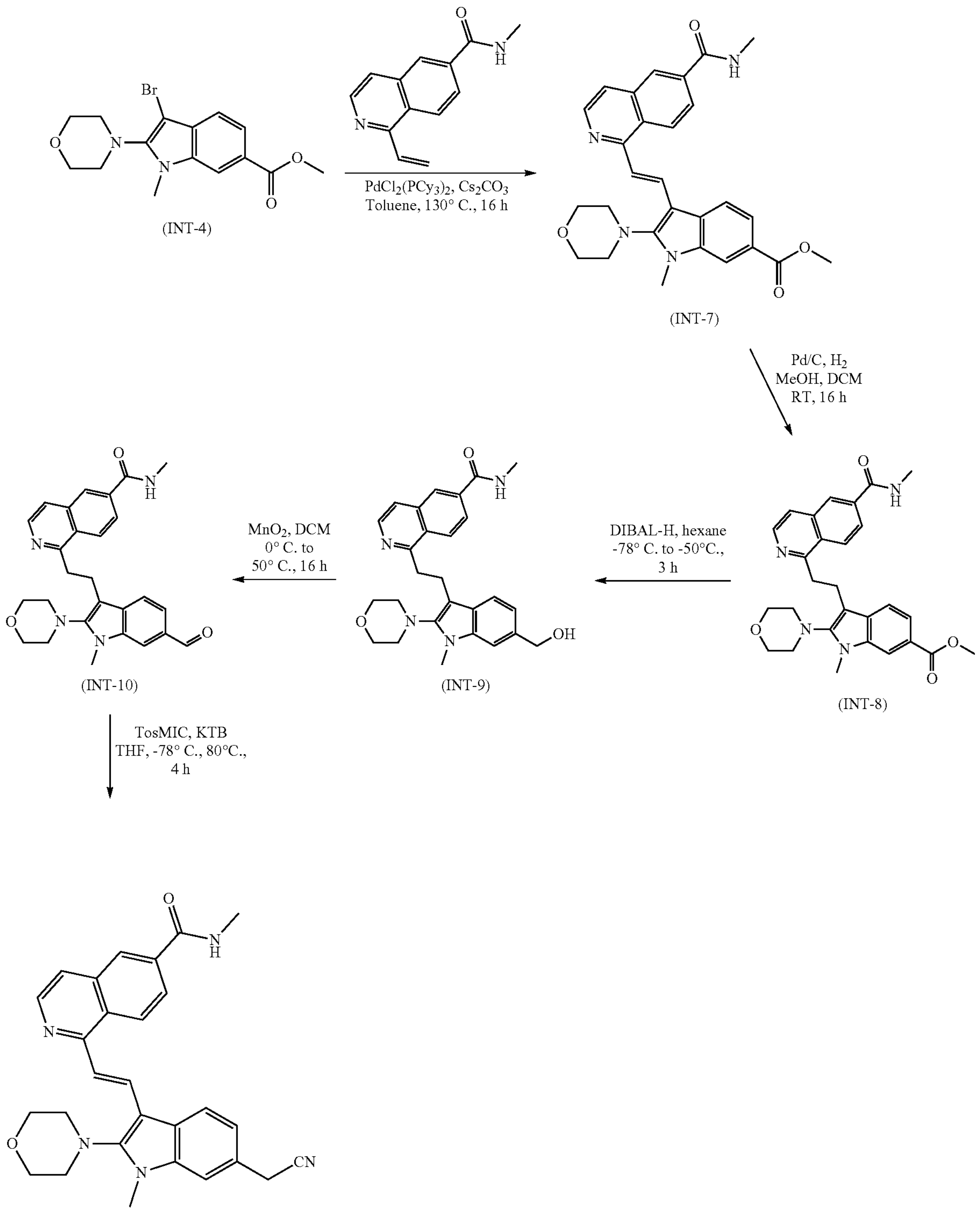
(19)

2-(3-(2-(6-Acetamidoisoquinolin-1-yl) ethyl)-1-methyl-2-morpholino-1H-indol-6-yl) acetonitrile (19) is synthesized according to the reaction of Scheme (6), as follows:

(a) Synthesis of methyl (E)-3-(2-(6-acetamidoisoquinolin-1-yl) vinyl)-1-methyl-2-morpholino-1H-indole-6-carboxylate (INT-7): Methyl 3-bromo-1-methyl-2-morpholino-1H-indole-6-carboxylate (INT-4), synthesized as described in Step 4 of Example 1, undergoes reaction with N-(1-vinyl-6-isoquinolinyl)acetamide in place of 1-vinylquinoline using the procedures, reagents, and reaction conditions described in Step 5, part (b), of Example 1. The reaction product obtained here is (INT-7) rather than (INT-5), as described in Step 5, part (b), of Example 1.

(b) Synthesis of methyl 3-(2-(6-acetamidoisoquinolin-1-yl) ethyl)-1-methyl-2-morpholino-1H-indole-6-carboxylate (INT-8): Methyl (E)-3-(2-(6-acetamidoisoquinolin-1-yl) vinyl)-1-methyl-2-morpholino-1H-indole-6-carboxylate (INT-7) is then used in place of (INT-5) used as a starting material in the reaction described in Step 6 of Example 1, but the procedures, reagents, and reaction conditions here are otherwise identical to those therein. The reaction product is (INT-8), shown in Scheme 6, rather than compound (1), obtained in Step 6 of Example 1.

(c) Synthesis of methyl 3-(2-(6-acetamidoisoquinolin-1-yl) ethyl)-1-methyl-2-morpholino-1H-indole-6-yl) methanol (INT-9): Methyl 3-(2-(6-acetamidoisoquinolin-1-yl) ethyl)-1-methyl-2-morpholino-1H-indole-6-carboxylate (INT-8) is then used in place of compound (1) as the reactant employed in the synthesis of Example 2, and diisobutylaluminum hydride (DIBAL-H) in hexane at −78° C. to −50° C. is used in lieu of LAH, but the procedures, reagents, and reaction conditions here are otherwise identical to those set forth in Example 2. The reaction product is (INT-9), as shown in Scheme 6.

(d) Synthesis of (3-(2-(6-acetamidoisoquinolin-1-yl) ethyl)-1-methyl-2-morpholino-1H-indole-6-carboxaldehyde (INT-10): Methyl 3-(2-(6-acetamidoisoquinolin-1-yl) ethyl)-1-methyl-2-morpholino-1H-indole-6-yl) methanol (INT-9) is converted to the aldehyde (INT-10) using the reaction described in Step 1 of Example 3, but substituting (INT-9) for compound (2) as reactant. The procedures, reagents, and reaction conditions are otherwise identical. The reaction product is (INT-10), as shown in Scheme 6.

(e) Synthesis of 2-(3-(2-(6-Acetamidoisoquinolin-1-yl) ethyl)-1-methyl-2-morpholino-1H-indol-6-yl) acetonitrile (19): The reaction of Example 3, Step 2, is repeated substituting (INT-10) for (INT-6) but with identical procedures, reagents, and reaction conditions. The reaction product that results here is the aryl-substituted N-alkyl indole (19).

Example 7

Synthesis of 2-(3-(2-(6-Acetylaminoisoquinolin-1-yl) ethyl)-1-methyl-2-morpholino-1H-indol-6-yl) acetonitrile (20)

Scheme (7)

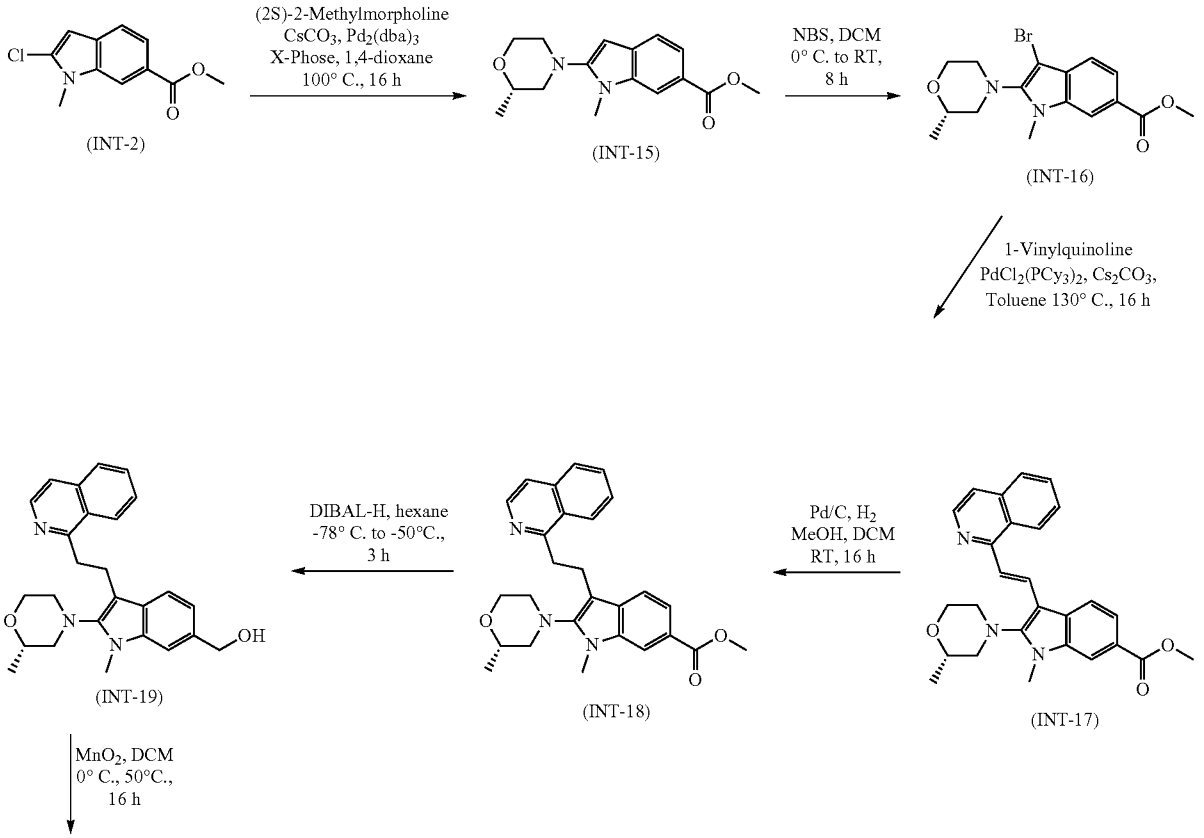

(INT-2) (INT-15) (INT-16) (INT-17) (INT-18) (INT-19)

-continued

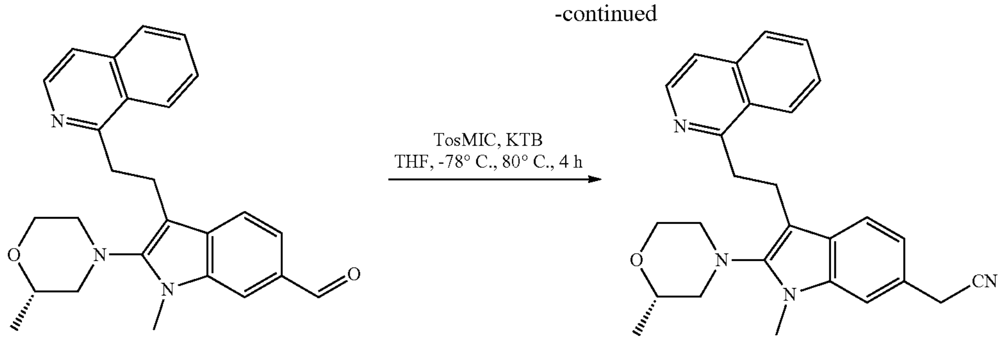

(INT-20) (22)

2-(3-(2-(6-acetylaminoisoquinolin-1-yl) ethyl)-1-methyl-2-morpholino-1H-indol-6-yl) acetonitrile (20) is synthesized according to the reaction of Scheme (7), as follows:

The aryl-substituted N-alkyl indole (20) is synthesized as described for the synthesis of compound (19) in Example 6, but substituting N-methyl-1-vinyl-6-isoquinolinecarboxamide (synthesized from N-methyl-6-isoquinolinecarboxamide as described in Gao et al. (2019) Org. Lett. 21(5): 1430-1433, the disclosure of which is incorporated by reference herein) for N-(1-vinyl-6-isoquinolinyl)acetamide in step (a) to generate (INT-11), as shown. The reactions of steps (b) through (e) are then followed using the same procedures, reagents, and reaction conditions, generating (INT-12), (INT-13), (INT-14), and compound (20).

Example 8

Synthesis of (3-(2-(Isoquinolin-1-yl) ethyl)-1-methyl-2-(6-methyl)morpholino-1H-indole-6-yl) acetonitrile (22)

Scheme (8)

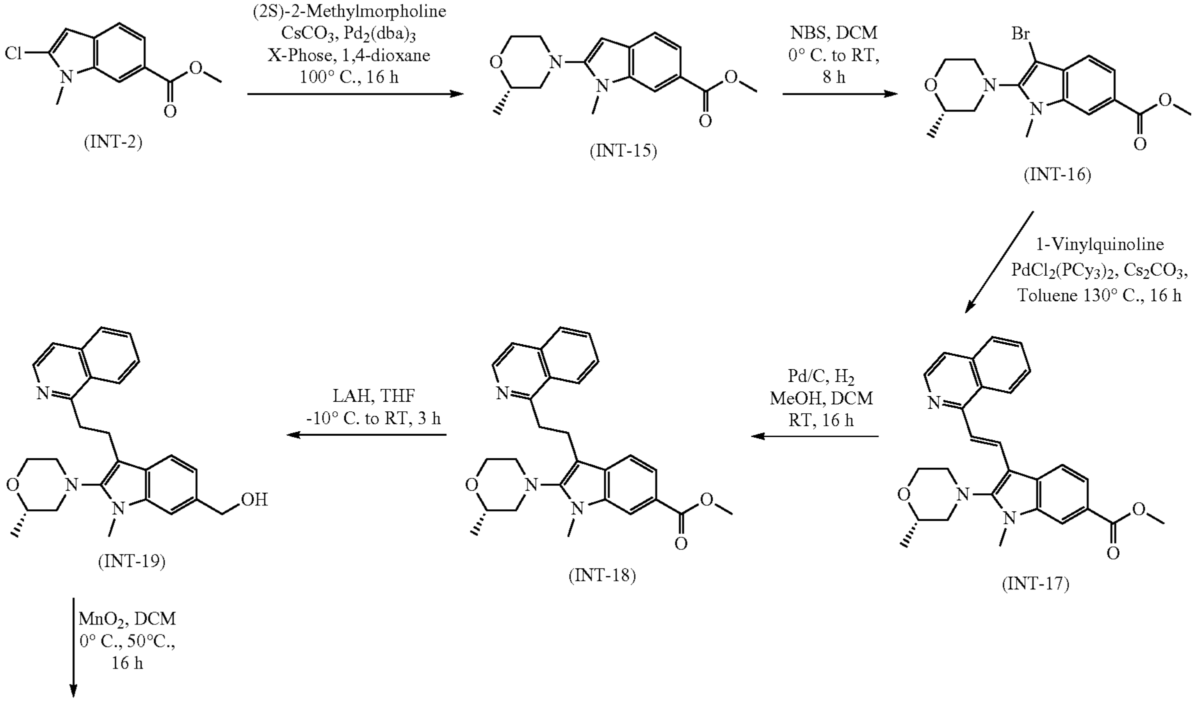

(INT-2) (INT-15) (INT-16) (INT-17) (INT-18) (INT-19)

-continued

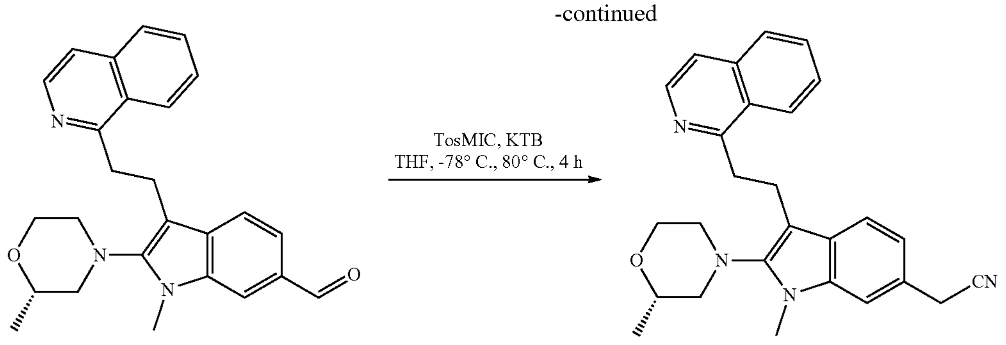

(INT-20) (22)

(3-(2-(Isoquinolin-1-yl) ethyl)-1-methyl-2-(6-methyl) morpholino-1H-indol-6-yl) acetonitrile (22) is synthesized according to the reaction shown in Scheme (8), as follows:

(a) Synthesis of methyl 1-methyl-2-(6-methyl)morpholino-1H-indole-6-carboxylate (INT-15): Methyl 2-chloro-1-methyl-1H-indole-6-carboxylate (INT-2), synthesized as described in Step 2 of Example 1, undergoes reaction as described in Step 3 of Example 1, but with (2S)-2-methylmorpholine substituted for morpholine. The procedures, reagents, and reaction conditions are otherwise identical to those used in Example 1, Step 3. The reaction product is methyl 1-methyl-2-(6-methyl)morpholino-1H-indole-6-carboxylate (INT-15).

(b) Bromination to give (INT-16): The intermediate (INT-15) is brominated using the procedures, reagents, and reaction conditions described in Step 4 of Example 1 to give methyl 3-bromo-1-methyl-2-(6-methyl)morpholino-1H-indole-6-carboxylate (INT-16).

(c) 1-vinylquinoline reaction: (INT-16) is reacted with 1-vinylquinoline as described in Step 5, part (b), of Example 1, using the procedures, reagents, and reaction conditions set forth therein. The reaction product obtained here is methyl (E)-3-(2-(isoquinolin-1-yl) vinyl)-1-methyl-2-(6-methyl)morpholino-1H-indole-6-carboxylate (INT-17), as shown in Scheme (8).

(d) Double bond hydrogenation: (INT-17) is hydrogenated with a Pd/C catalyst as described in Step 6 of Example 1, using the procedures, reagents, and reaction conditions set forth therein. The reaction product obtained here is methyl 3-(2-(isoquinolin-1-yl) ethyl-1-methyl-2-(6-methyl)morpholino-1H-indole-6-carboxylate (INT-18), as shown in Scheme (8).

(e) Reduction of the ester to the alcohol: (INT-18), an ester, is reduced to the corresponding alcohol using lithium aluminum hydride, as described in Example 2. The same procedures, reagents, and reaction conditions are used here. The reaction product is (3-(2-(isoquinolin-1-yl) ethyl)-1-methyl-2-(6-methyl)morpholino-1H-indol-6-yl) methanol (INT-19).

(f) Synthesis of aldehyde (INT-20): (INT-19) is converted to the corresponding aldehyde using the selective oxidation procedure of Example 3, Step 1. The same procedures, reagents, and reaction conditions are used, resulting in the reaction product 3-(2-(isoquinolin-1-yl) ethyl)-1-methyl-2-(6-methyl)morpholino-1H-indole-6-carbaldehyde (INT-20).

(g) Conversion of the aldehyde to nitrile (22): The intermediate (INT-20) is substituted for (INT-6) in the reaction described in Step 2 of Example 3. The procedures, reagents, and reaction conditions used here are identical, resulting in the reaction product 2-(3-(2-(isoquinolin-1-yl) ethyl)-1-methyl-2-(6-methyl)morpholino-1H-indol-6-yl) acetonitrile (22).

Example 9

Synthesis of {3-[2-(isoquinolin-1-yl)ethyl]-1-methyl-2-[(1R,5R)-3-oxa-8-azabicyclo[3.2.1]oct-8-yl]-1H-indol-6-yl}acetonitrile (23)

Scheme (9)

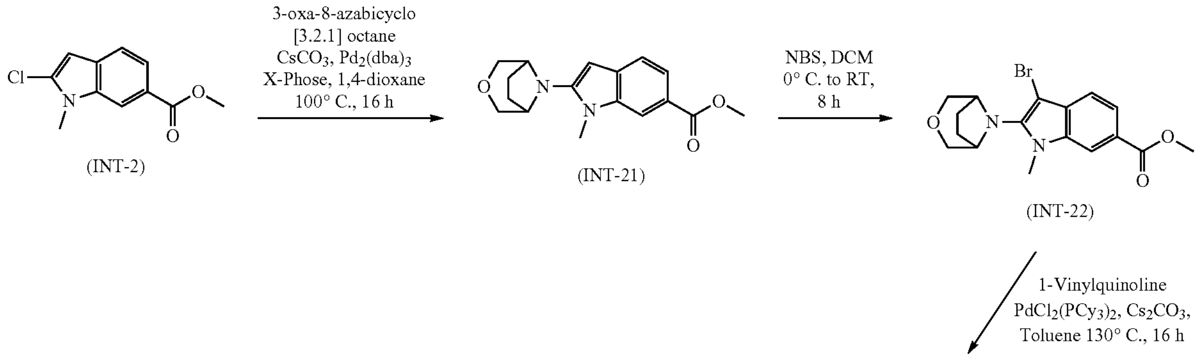

(INT-2) (INT-21) (INT-22)

-continued

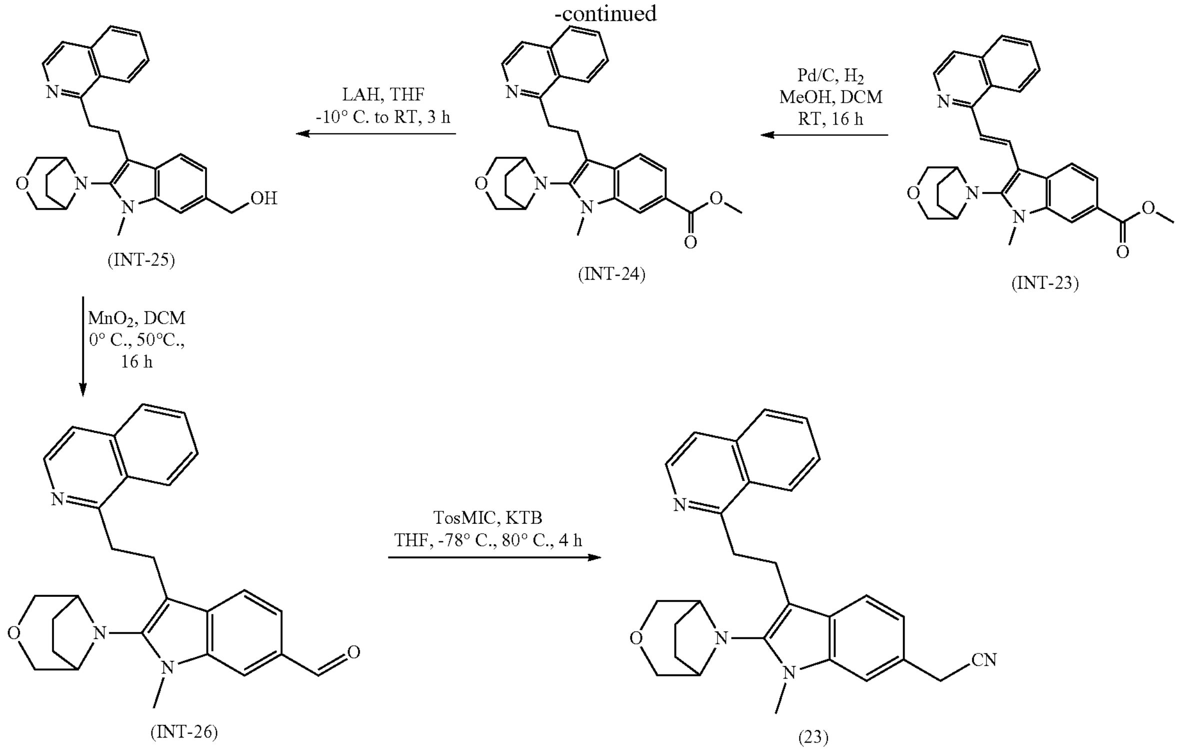

(INT-23) (INT-24) (INT-25) (INT-26) (23)

{3-[2-(isoquinolin-1-yl)ethyl]-1-methyl-2-[(1R,5R)-3-oxa-8-azabicyclo[3.2.1]oct-8-yl]-1H-indol-6-yl}acetonitrile (23) is synthesized according to the reaction of Scheme (9), as described for the synthesis of compound (22) in Example 8, but substituting 3-oxa-8-azabicyclo[3.2.1]octane (Enamine US, Inc.), for morpholine at the outset in the reaction with (INT-2). The reactions of steps (a) through (g) of Example 8 are repeated here using the same procedures, reagents, and reaction conditions to generate (INT-21), (INT-22), (INT-23), (INT-24), (INT-25), and (INT-26), as shown in Scheme (9). The reaction product resulting from conversion of the aldehyde (INT-26) to the corresponding nitrile is the aryl-substituted N-alkyl indole (23).

Example 10

Synthesis of 2-(3-(2-(Isoquinolin-1-yl) ethyl)-1-methyl-2-morpholino-1H-indol-6-yl) acetamide (25)

Scheme (10)

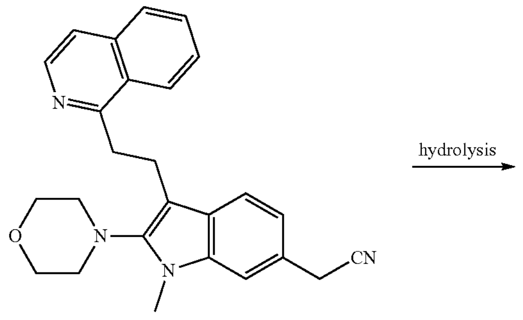

(3)

-continued

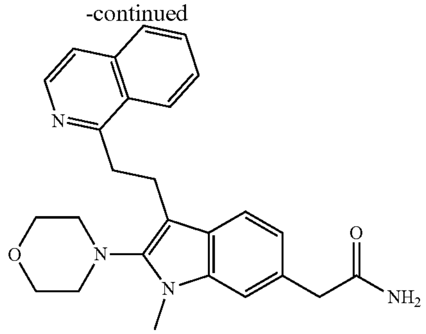

(25)

The procedure of Scheme (10) is used to synthesize 2-(3-(2-(isoquinolin-1-yl) ethyl)-1-methyl-2-morpholino-1H-indol-6-yl) acetamide (25). The reactant here is 2-(3-(2-(isoquinolin-1-yl) ethyl)-1-methyl-2-morpholino-1H-indol-6-yl) acetonitrile (3) (synthesized as described in Example 3), which is hydrolyzed in the presence of acid or base using standard hydrolysis procedures known in the art and described, for example, in March's Advanced Organic Chemistry: Reactions, Mechanisms, and Structure, Smith, B. et al., eds. (New York: John Wiley & Sons, Inc., 2001).

Example 11

Radioligand Binding Assay and Data

Compound plates were prepared by diluting a 5 mM DMSO stock solution of the reference compound (CP55940, CAS Number 83003-12-7, 5-(1,1-dimethylheptyl)-2-[(1R, 2R,5R)-5-hydroxy-2-(3-hydroxypropyl)cyclohexyl]phenol) in a series of five-fold dilutions to generate eight distinct concentrations of the aryl-substituted N-alkyl indoles (1) through (5) undergoing evaluation. Stock solutions of the test compound were also prepared in DMSO. A volume of 750 nL from each reference and test compound was transferred to a 96-well plate, followed by the addition of 150 μL of assay buffer to achieve a 5× working concentration. The plates were then centrifuged at 1,000 rpm for 30 seconds and mixed at 600 rpm for 5 minutes at room temperature.

Separately, each well of UniFilter-96 GF/C plates was treated with 50 μL of 0.5% (v/v) polyethyleneimine (PEI), sealed, and incubated at 4° C. for 3 hours. The plates underwent two washes with ice-cold buffer before use. Cell membranes were suspended in assay buffer and dispensed into 96-round deep-well plates at a final concentration of 10 μg per well (330 μL per well). Next, 110 μL of each test compound concentration and 110 μL of each reference compound concentration were transferred from the compound plate to the deep-well plates. Radiolabeled ligands were prepared in assay buffer, and 110 μL of this solution was added to each well to obtain a 5× working concentration. The final concentrations of $[^3H]$-CP55940 were 2 nM for CB1 and 1.25 nM for CB2.

Following compound and radioligand addition, the plates were centrifuged at 1,000 rpm for 30 seconds and shaken at 600 rpm for 5 minutes at room temperature. They were then sealed and incubated at 30° C. for 90 minutes. Incubation was terminated by vacuum filtration through GF/C plates, followed by four washes with ice-cold buffer. The plates were dried at 37° C. for 45 minutes, after which 40 μL of scintillation cocktail was added to each well. Radioactivity levels were measured using a MicroBeta2 microplate counter (PerkinElmer, Waltham, MA, USA).

The IC50 values of compounds (1) through (5) determined in the radioligand binding assay are set forth in the following Table 1:

TABLE 1

| Compound | CB1 | CB2 |
|---|---|---|
| (1) | >10000 nM | >10000 nM |
| (2) | >10000 nM | 4856 nM |
| (3) | 5063 nM | 6426 nM |
| (4) | >10000 nM | >10000 nM |
| (5) | >10000 nM | >10000 nM |

Example 12

Evaluation of (2), (3) and (4) in Treating Pain and Inflammation In Vivo

Experimental Procedure:

Male CD-1 mice (n=85, 18-20 g; Envigo) were housed under standard conditions with ad libitum access to food and water. After a 3-day acclimation period, mice were weight-matched into eight groups (n=10/group). Inflammation was induced via subcutaneous injection of 1.2% carrageenan (20 μL) into the left hind paw. The test compounds, aryl-substituted N-alkyl indoles (2), (3), and (4), and vehicle (7.8% Tween 80 in saline) were administered intraperitoneally 0.5 h prior to carrageenan. Carprofen (30 mg/kg) and morphine (5 mg/kg) were administered subcutaneously.

Assessments:

Ankle Diameter: Measured using a digital micrometer at baseline and 2, 4, 6, and 8 h post-carrageenan. Percent change from baseline and left-right differences were calculated.

Thermal Hyperalgesia (Hargreaves Test): Baseline latency was established on Day 3. Post-treatment response times were recorded using a heated apparatus (30° C.; 20 s cutoff) at 1 and 3 h post carrageenan.

Data are expressed as mean±SEM. Ordinary one-way ANOVA with Dunnett's post hoc test compared treatment groups to vehicle controls. Significance was set at $p<0.05$ (GraphPad Prism 10.3.1). All procedures adhered to institutional guidelines, and euthanasia was performed under isoflurane anesthesia.

Figure 2:
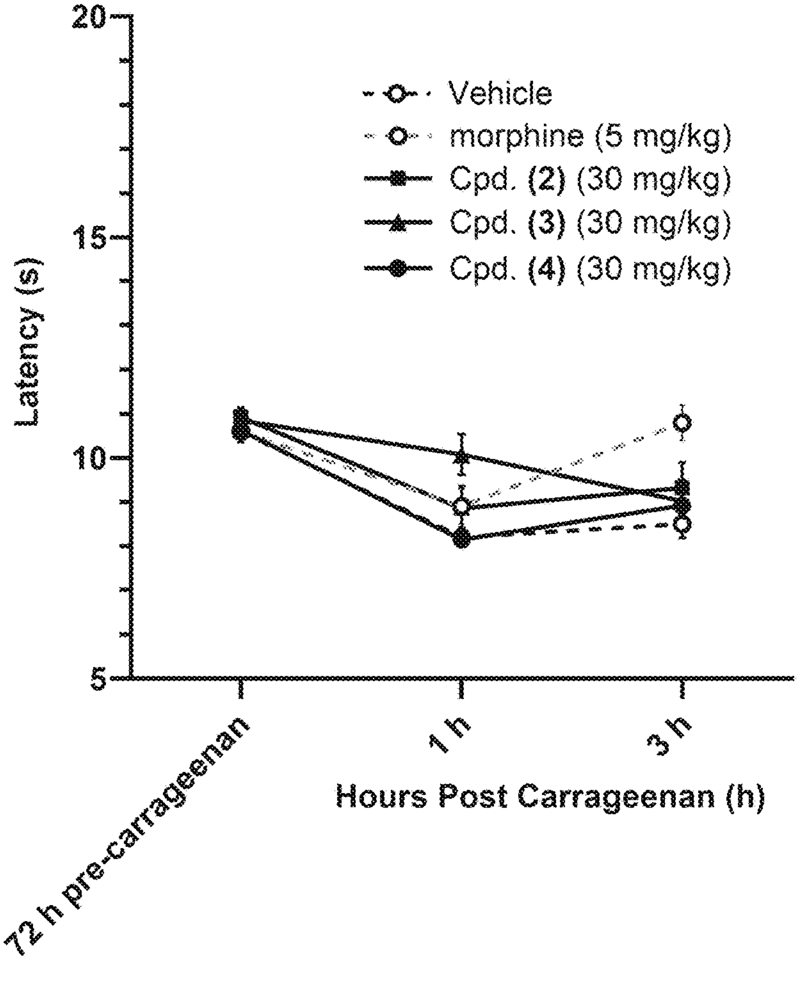
FIG. 2 is a graph indicating the efficacy of compounds (2), (3), and (4) in reducing thermally induced pain in mice using the Hargreaves test and provides a comparison with morphine, as also evaluated according to the description in Example 12.

The results are illustrated in the graphs of FIGS. 1 and 2. As illustrated therein, compounds (2), (3), and (4) exhibited potent efficacy in treating pain and inflammation compared to carprofen and morphine.

Example 13

In Vivo Pharmacokinetic Evaluation

Animals and Study Design:

Male CD-1 mice (6-8 weeks old, 20.5-25.1 g) were administered (3) via intraperitoneal (IP) injection at three dose levels: 3, 30, and 100 mg/kg (n=3 per group). Dosing formulations were prepared as suspensions in 7.8% Tween 80 (polysorbate 80) and saline, with concentrations of 0.6, 6, and 20 mg/mL, respectively. Animals were fasted prior to dosing, and blood samples (~0.03 mL) were collected from the dorsal metatarsal vein at 0.25, 0.5, 1, 2, 4, 6, 8, and 24 hours post-dose. Plasma was separated via centrifugation (4000×g, 5 min, 4° C.) and stored at −75±15° C. until analysis.

Plasma concentrations of compound (3) were quantified using a validated LC-MS/MS method. Samples were protein-precipitated with acetonitrile containing dexamethasone as the internal standard. Chromatographic separation was achieved on a Phenomenex® Kinetex C18 column (2.6 μm, 30×2.1 mm) with a gradient mobile phase (5-95% acetonitrile in 0.1% formic acid). Quantification employed a Shimadzu LC-40D system coupled to an AB Sciex API 6500 mass spectrometer, operating in MRM mode (Q1/Q3: 416.17/176.20 Da). Calibration curves (0.5-1000 ng/mL) and quality controls demonstrated accuracy within 88.5-110%. Non-compartmental analysis (WinNonlin 8.3) was used to estimate parameters, including half-life (T½) maximum concentration (Cmax), area under the curve (AUClast, AUCinf), and mean residence time (MRT).

The pharmacokinetic data obtained at the 30 mg/kg dosage level is shown in Table 2:

TABLE 2

Summary of PK data at 30 mg/kg dose

| PK parameters | Unit | Cpd. (3) (30 mg/kg, i.p.) |
|---|---|---|
| $T_{1/2}$ | h | 7.93 |
| $T_{max}$ | h | 0.250 |
| $C_{max}$ | nM | 1705 |
| $AUC_{last}$ | h * nM | 2006 |
| $AUC_{Inf}$ | h * nM | 2061 |
| $AUC_{_\%Extrap_}$obs | % | 2.66 |
| $MRT_{Inf_}$obs | h | 2.97 |
| $AUC_{last}$/D | h * nM/(mg/kg) | 66.9 |

Figure 3:
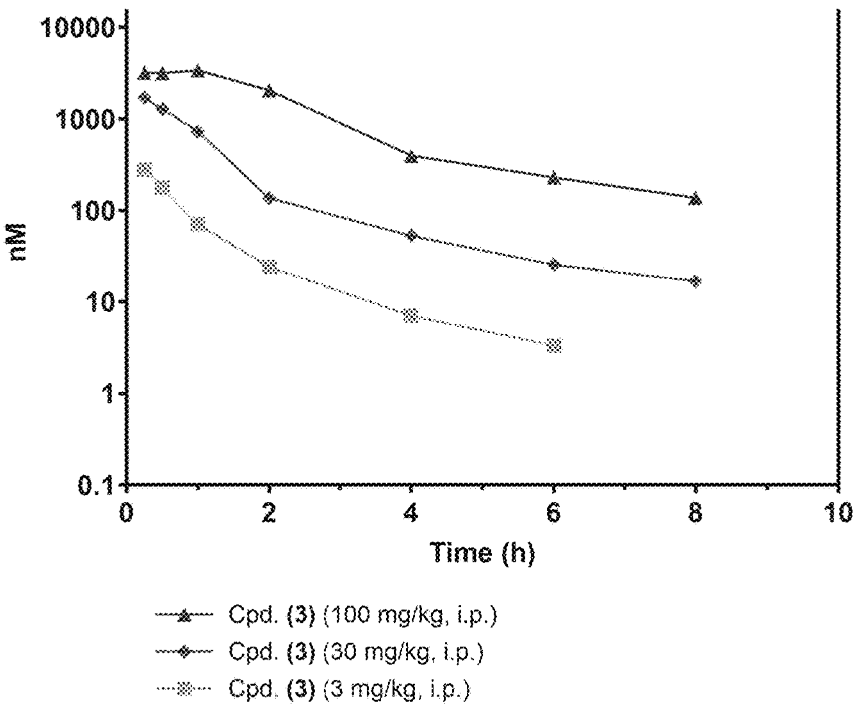
FIG. 3 is a graph showing the pharmacokinetic profile obtained after administration of compound (3) to mice at different doses, determined as described in Example 13.

The pharmacokinetic data obtained was plotted and is shown in FIG. 3. As may be seen, compound (3) follows approximately linear pharmacokinetics in the 3-100 mg/kg dose range. This is advantageous because it simplifies dose optimization and provides predictable drug behavior across different doses. Linear pharmacokinetics also helps with human dose prediction necessary to choose the starting dose in the clinic.

Example 14

CB1 and CB2 Agonist Assays

Arrestin assay: For arrestin CB1 and CB2 agonist assays, the PathHunter® 3-Arrestin CHO-K1 cells, which overexpress the CB1 or CB2 receptors, were cultivated from frozen stocks using the standard protocols supplied by Eurofins, adhering to the guidelines in the cell line manual for cell cultivation (covering aspects such as culture media, supplements, and cell handling) as well as for conducting the assay and detecting signals. Cells were dispensed at a density of 5000 cells per 20 μL into white-walled, 384-well plates and then incubated at 37° C. overnight in cell plating reagent. Subsequently, a stock solution of the ligand in DMSO at 1 mg/mL was prepared, from which intermediate concentrations of the compound were derived through a series of ten 3-fold serial dilutions using dilution buffer in a separate dilution plate. Each dilution was prepared at a 5× concentration relative to the intended final concentrations for screening. Next, 5 μL of these samples was introduced into the cells, achieving a maximum final concentration of 10 μM for the test compound. Cells were incubated at 37° C. for 90 min in an atmosphere containing 5% CO2. To generate the assay signal, 12.5 μL of working detection solution was added to the cells, which were then left to incubate for an hour at room temperature in the dark. The signal detection was carried out using a PerkinElmer Envision instrument to measure chemiluminescence.

cAMP assay: For the cAMP CB1 and CB2 agonist assays, the cAMP Hunter™ CHO-K1 cells, which overexpress CB1 and CB2 receptors, were cultivated from frozen stocks using the standard protocols supplied by Eurofins, adhering to the guidelines in the cell line manual for cell cultivation (covering aspects such as culture media, supplements, and cell handling) as well as for conducting the assay and detecting signals. Cells were seeded in a total volume of 20 μL (10,000 cells) into white-walled, 384-well microplates and incubated at 37° C. in cell plating reagent overnight. Before adding ligands, media were aspirated from cells and replaced with 10 μL cAMP assay buffer. Stock DMSO solution at 1 mg/mL concentration of test compounds was diluted in cAMP assay buffer to generate a 3× sample containing 3× EC80 forskolin. Five μL of sample solution was added to cells (highest final concentration=3 μM) and incubated at 37° C. for 30 min. The assay signal was generated through incubation with 5 μL antibody solution and 20 μL working cAMP detection solution for one hour (room temperature, dark), followed by incubation with 20 μL cAMP solution A for three hours at room temperature in the dark. Microplates were read following signal generation with a PerkinElmer Envision instrument for chemiluminescent signal detection.

Table 4 provides the EC50 values of compounds (2), (3), and (4) obtained in the CB1 and CB2 agonist assays:

TABLE 4

| | CB1 | | | CB2 | | |
|---|---|---|---|---|---|---|
| Cpd. | cAMP | B-arrestin | Functional activity | cAMP | B-arrestin | Functional activity |
| (2) | >3000 nM | >3000 nM | Partial agonist | >3000 nM | >3000 nM | Partial agonist |
| (3) | 1174 nM | >3000 nM | Biased partial agonist | 109 nM | 370 nM | Inverse agonist |
| (4) | 763 nM | >3000 nM | Biased partial agonist | >3000 nM | >3000 nM | Biased partial agonist |

Example 15

Endometriosis Study

Female C57BL/6J mice (7-8 weeks old) housed under controlled conditions (20-25° C., 40-70% humidity, 12-h light/dark cycle) with ad libitum access to food and water. Animals were acclimated for 7 days prior to the study. To induce endometriosis, estrous cycle stages were identified in donor animals via daily vaginal smears, and proestrus/estrus-phase animals were selected. Donor mice were euthanized and their uterine horns harvested. Uterine tissue was trimmed and cut into 2×2 mm fragments, which were then sutured onto the abdominal wall of recipient mice under anesthesia via midline laparotomy (four fragments per mouse). Sham-operated animals received adipose tissue grafts instead of endometrial tissue, and healthy controls underwent laparotomy without any tissue transplantation. Post-operative care included administration of analgesics (meloxicam and butorphanol) and antibiotics (ampicillin) for 2 days. Estradiol (17β-estradiol, 25 μg/kg) was administered subcutaneously every 3 days for a total of nine doses to support endometrial graft survival.

Four weeks post-transplantation, endometriotic lesions were assessed via caliper measurement. Mice with established lesions were randomized into 13 groups (n=6-11/group) with equivalent lesion volumes. Treatment with compound (3) was carried out at the dose indicated in FIG. 4 (in the figure, "EM" represents endometriosis), with carprofen treatment and no treatment (administration of formulation free of active agent) carried out for purposes of comparison. The formulations were administered daily, intraperitoneally (i.p.) or subcutaneously (s.c.), for four weeks. All formulations used 7.8% Tween 80 in saline for test articles and saline alone for reference and vehicle controls.

von Frey mechanical allodynia was assessed on days 36, 43, 50, 57, and 62 using calibrated filaments applied to the left hind paw and abdomen. Thresholds were calculated using the Dixon up-down method. Following the final treatment, mice in estrus phase were selected for terminal procedures within 2-4 hours after dosing. Animals were euthanized via $CO_2$ inhalation followed by cervical dislocation. Peritoneal lavage fluid, blood, and uterine grafts were collected. Grafts were measured, weighed, photographed, and preserved in 10% formalin for future analysis.

Figure 4:
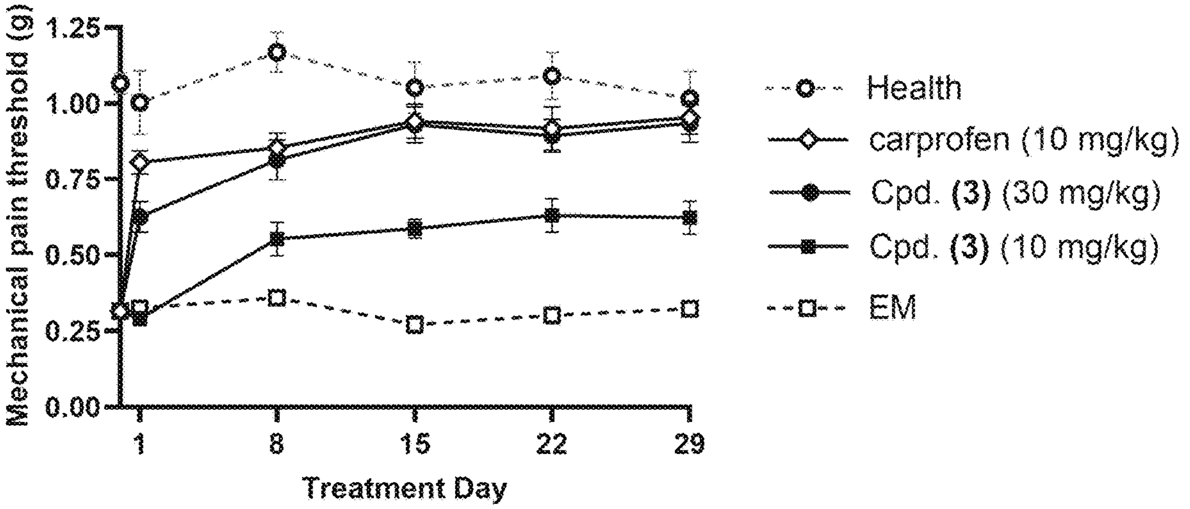
FIG. 4 provides, in graph form, the results of the experiment of Example 15 conducted to evaluate the effect of compound (3) on endometrial pain in mice.

As indicated in the results illustrated in the graph of FIG. 4, compound (3) displayed potent pain reduction comparable to that seen with the NSAID carprofen.

Example 16

Further Evaluation of Aryl-Substituted N-Alkyl Indole Compounds as Drug Candidates Receptor affinities, log P, topological polar surface area (TPSA), hydrogen bond donors (HBD), and molecular weight of several aryl-substituted N-alkyl indoles having the structure of formula (I) were calculated and are set forth in Table 4. Receptor affinities were calculated using Boltz-2, an open source structural biology foundation model described, inter alia, by Passaro et al., "Boltz-2: Towards Accurate and Efficient Binding Affinity Prediction," posted Jun. 18, 2025 as a bioRxiv preprint doi: https://doi.org/10.1101/2025.06.14.659707. Log P, TPSA, and HBD were calculated using ADMET-AI; see Swanson et al., "ADMET-AI: A Machine Learning ADMET Platform for Evaluation of Large Scale Chemical Libraries," posted Dec. 28, 2023 as a bioRxiv preprint doi: https://doi.org/10.1101/2023.12.28.573531.

TABLE 4

| Cpd. No. | CB1 affinity (calc) | CB2 affinity (calc) | log P | TPSA ($Å^2$) | HBD | MW |
|---|---|---|---|---|---|---|
| (19) | 499 nM | 791 nM | 3.774 | 83.18 | 1 | 467.6 |
| (20) | 215 nM | 785 nM | 4.373 | 83.18 | 1 | 467.6 |
| (22) | 213 nM | 110 nM | 4.803 | 54.08 | 0 | 424.6 |
| (23) | 242 nM | 137 nM | 4.945 | 54.08 | 0 | 436.6 |
| (25) | 1000 nM | 562 nM | 3.376 | 73.38 | 1 | 428.5 |

The following Examples 17-84 describe preparation of pharmaceutical dosage forms for administration of an aryl-substituted N-alkyl indole of the invention.

Example 17

Gummy Formulation

A gummy formulation of the invention is prepared by combining (3) with sugar, tapioca syrup, water, pectin, flavoring agent, citric acid, fruit and vegetable juice colorant, coconut oil, and carnauba wax. The mixture is heated until it becomes flowable, and is then poured into individual gummy molds with each mold sized to provide a 4 g gummy. After molding, the gummies are cooled and dried, e.g., by air convection in convection chambers, to achieve a texture that is somewhat dry and sticky. The amount of (3) in each 4 g gummy is 10 mg to 200 mg (0.25 wt. % to 5.0 wt. %), and the amount of sugar in each gummy is 1.58 g (39.5 wt. %). Pectin, the gelling agent, represents 5.0 wt. % of the gummy.

Example 18

Gummy Formulation

The method of Example 17 is repeated, with the non-sugar sweetener erythritol substituted for sugar. The amount of (3) in each 4 g gummy is 10 mg to 200 mg (0.25 wt. % to 5.0 wt. %), and the amount of erythritol in each 4 g gummy is 1.58 g (39.5 wt. %). Pectin, the gelling agent, represents 5.0 wt. % of the gummy.

Example 19

Gummy Formulation

The method of Example 17 is repeated, with the non-sugar sweetener stevia substituted for sugar. The amount of (3) in each 4 g gummy is 10 mg to 200 mg (0.25 wt. % to 5.0 wt. %), and the amount of stevia in each 4 g gummy is 1.58 g (39.5 wt. %). Pectin, the gelling agent, represents 5.0 wt. % of the gummy.

Example 20

Gummy Formulation

The method of Example 17 is repeated, with the non-sugar sweeteners stevia and erythritol substituted for sugar. The amount of (3) in each 4 g gummy is 10 mg to 200 mg (0.25 wt. % to 5.0 wt. %), and the combined amounts of erythritol and stevia in each 4 g gummy is 1.58 g (39.5 wt. %). Pectin, the gelling agent, represents 5.0 wt. % of the gummy.

Example 21

Gummy Formulation

The method of Example 17 is repeated, with agar gum substituted for pectin as the gelling agent. The amount of (3) in each 4 g gummy is 10 mg to 200 mg (0.25 wt. % to 5.0 wt. %), and the amount of sugar in each 4 g gummy is 1.58 g (39.5 wt. %). Agar gum, the gelling agent, represents 5.0 wt. % of the gummy.

Example 22

Gummy Formulation

The method of Example 18 is repeated, with agar gum substituted for pectin as the gelling agent. The amount of (3) in each 4 g gummy is 10 mg to 200 mg (0.25 wt. % to 5.0 wt. %), and the amount of erythritol in each 4 g gummy is 1.58 g (39.5 wt. %). Agar gum, the gelling agent, represents 5.0 wt. % of the gummy.

Example 23

Gummy Formulation

The method of Example 19 is repeated, with agar gum substituted for pectin as the gelling agent. The amount of (3) in each 4 g gummy is 10 mg to 200 mg (0.25 wt. % to 5.0 wt. %), and the amount of stevia in each 4 g gummy is 1.58 g (39.5 wt. %). Agar gum, the gelling agent, represents 5.0 wt. % of the gummy.

Example 24

Gummy Formulation

The method of Example 20 is repeated, with agar gum substituted for pectin as the gelling agent. The amount of (3) in each 4 g gummy is 10 mg to 200 mg (0.25 wt. % to 5.0 wt. %), and the combined amount of erythritol and stevia in each 4 g gummy is 1.58 g (39.5 wt. %). Agar gum, the gelling agent, represents 5.0 wt. % of the gummy.

Example 25

Gummy Formulation

The method of Example 17 is repeated, with carageenan substituted for pectin as the gelling agent. The amount of (3) in each 4 g gummy is 10 mg to 200 mg (0.25 wt. % to 5.0 wt. %), and the amount of sugar in each 4 g gummy is 1.58 g (39.5 wt. %). Carageenan, the gelling agent, represents 5.0 wt. % of the gummy.

Example 26

Gummy Formulation

The method of Example 18 is repeated, with carageenan substituted for pectin as the gelling agent. The amount of (3) in each 4 g gummy is 10 mg to 200 mg (0.25 wt. % to 5.0 wt. %), and the amount of erythritol in each 4 g gummy is 1.58 g (39.5 wt. %). Carageenan, the gelling agent, represents 5.0 wt. % of the gummy.

Example 27

Gummy Formulation

The method of Example 19 is repeated, with carageenan substituted for pectin as the gelling agent. The amount of (3) in each 4 g gummy is 10 mg to 200 mg (0.25 wt. % to 5.0 wt. %), and the amount of stevia in each 4 g gummy is 1.58 g (39.5 wt. %). Carageenan, the gelling agent, represents 5.0 wt. % of the gummy.

Example 28

Gummy Formulation

The method of Example 20 is repeated, with carageenan substituted for pectin as the gelling agent. The amount of (3) in each 4 g gummy is 10 mg to 200 mg (0.25 wt. % to 5.0 wt. %), and the combined amount of erythritol and stevia in each 4 g gummy is 1.58 g (39.5 wt. %). Carageenan, the gelling agent, represents 5.0 wt. % of the gummy.

Examples 29-77

Gummy Formulations

The methods of Examples 12-23 are repeated with compounds (1), (2), (4), and (5) in place of compound (3).

It will be appreciated by those of ordinary skill in the art that additional sweeteners, gelling agents, and excipients can be substituted for those delineated in the foregoing examples. Furthermore, any aryl-substituted N-alkyl indole of the invention can be substituted for compounds (1) through (5).

Example 78

Compressed Tablet Dosage Form

A compressed tablet formulated for oral administration of (3) is prepared by combining the compound with microcrystalline cellulose as a filler; lactose, also as a filler; magnesium stearate as a lubricant; hydroxypropylmethylcellulose as a binder; and optionally a disintegrant such as potato starch, croscarmelose, or sodium starch glycolate. The mixture is compacted into individual tablets using conventional means, e.g., direct compression (DC). The composition of each tablet is 0.25 wt. % to 50 wt. % aryl-substituted N-alkyl indole; 15 wt. % to 75 wt. % filler; 0.1 wt. % to 1 wt. % lubricant; 0.5 wt. % to 5 wt. % binder; and zero to 10 wt. % disintegrant.

Examples 79-82

Compressed Tablet Dosage Form

The method and components of Example 78 are repeated with compounds (1), (2), (4), and (5) substituted for compound (3) as the active agent (Examples 79, 80, 81, and 82, respectively).

Other fillers, lubricants, binders, disintegrants, may be substituted for those set forth in Examples 1-77 by reference to Section III of the Detailed Description or to the pertinent literature and texts relating to the manufacture of pharmaceutical dosage forms.

Example 83

Intravaginal Suppository

A suppository is formulated using conventional formulation techniques, e.g., molding, cold compression, or hand rolling, as described in Remington's, supra, and elsewhere. An aryl-substituted N-alkyl indole of the invention, e.g., (3), is incorporated into a base of cocoa butter, polyethylene glycol(s), and/or esterified, fractionated, or hydrogenated vegetable oil(s), or the like, in an amount to provide a suppository in which active agent represents 0.25 wt. % to 50 wt. % of the dosage form and the suppository base represents 15 wt. % to 75 wt. % of the dosage form.

Example 84

Cream

A pharmaceutical cream containing an aryl-substituted N-alkyl indole of the invention, e.g., (3), is prepared as follows. Separate oil and water phases are prepared, with the oil phase containing wax, emollients, oils, or the like, and the water phase composed of water and water-soluble ingredients such as emulsifiers and thickeners. The two phases are combined under controlled conditions using high-speed mixing or homogenization, to create a stable emulsion. The selected active agent is dispersed therein and even distribution throughout the formulation is ensured. The amount of the selected active agent added to the emulsion is sufficient to provide a cream formulation with a concentration of 0.25 wt. % to 50 wt. % of the aryl-substituted N-alkyl indole.

The invention claimed is:

1. An aryl-substituted N-alkyl indole having the structure of formula (I)

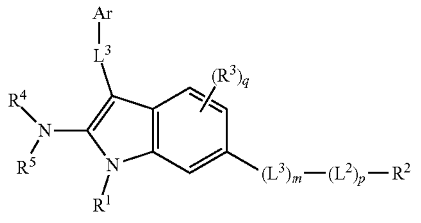

wherein:

m, p, and q are independently selected from zero and 1;

$L^1$ is selected from $C_1$-$C_3$ alkylene and $C_2$-$C_3$ alkenylene, and is optionally substituted with hydroxyl, $C_1$-$C_3$ alkoxy, or halo;

$L^2$ is selected from —(CO)— and —($SO_2$)—;

$L^3$ is selected from $C_2$-$C_3$ alkylene and $C_2$-$C_3$ alkenylene, and is optionally substituted with hydroxyl, $C_1$-$C_3$ alkoxy, or halo;

$R^1$ is H or $C_1$-$C_3$ alkyl;

$R^2$ is selected from $C_1$-$C_3$ alkyl, $C_2$-$C_3$ alkenyl, halogenated $C_1$-$C_3$ alkyl, halogenated $C_2$-$C_3$ alkenyl, hydroxyl, hydroxyl-substituted $C_1$-$C_3$ alkyl, $C_1$-$C_3$ alkoxy, cyano, amino, mono-$C_1$-$C_3$ alkyl-substituted amino, di-$C_1$-$C_3$ alkyl-substituted amino, and morpholinyl;

$R^3$ is selected from hydroxyl, $C_1$-$C_3$ alkoxy, and amino;

$R^4$ and $R^5$ are independently selected from H and $C_1$-$C_3$ alkyl or are linked to form an aliphatic N-heterocycle optionally substituted with one or two non-hydrogen substituents selected from $C_1$-$C_3$ alkyl, hydroxyl, and $C_1$-$C_3$ alkoxy, or wherein two non-hydrogen substituents on the aliphatic N-heterocycle are linked to form a bridged bicyclic moiety comprising a 1-, 2-, or 3-carbon atom bridge; and Ar is bicyclic N-heteroaryl bound to $L^3$ through a ring carbon atom and is optionally substituted with at least one substituent selected from hydroxyl, amido, mono-($C_1$-$C_3$ alkyl)amido, di-($C_1$-$C_3$ alkyl)amido, and $C_2$-$C_3$ acylamino.

2. The aryl-substituted N-alkyl indole of claim 1, wherein p and q are zero.

3. The aryl-substituted N-alkyl indole of claim 2, wherein:

m is 1;

$L^1$ is $C_1$-$C_3$ alkylene;

$L^3$ is —$CH_2CH_2$—;

$R^1$ is $C_1$-$C_3$ alkyl;

$R^2$ is cyano;

$R^4$ and $R^5$ are linked to form a morpholinyl group optionally substituted with one or two $C_1$-$C_3$ alkyl groups or with two substituents that together form a bridged bicyclic moiety having a 2-carbon atom bridge; and Ar is selected from quinolinyl, isoquinolinyl, tetrahydroquinolinyl, and tetrahydroisoquinolinyl, and is optionally substituted with a hydroxyl, amido, methylamido, dimethylamido, or acetylamino group.

4. The aryl-substituted N-alkyl indole of claim 3, wherein $L^1$ is —$CH_2$—, $R^1$ is methyl, $R^4$ and $R^5$ are linked to form an unsubstituted morpholinyl group, and Ar is isoquinolinyl optionally substituted with a hydroxyl, methylamido, or acetylamino group.

5. The aryl-substituted N-alkyl indole of claim 4, wherein Ar is unsubstituted isoquinolinyl.

6. The aryl-substituted N-alkyl indole of claim 1, wherein:

m is zero or 1;

p is 1;

q is zero;

$L^1$ is $C_1$-$C_3$ alkylene;

$L^3$ is —$CH_2CH_2$—;

$R^1$ is $C_1$-$C_3$ alkyl;

$R^2$ is selected from hydroxyl, amino, and $C_1$-$C_3$ alkoxy;

$R^4$ and $R^5$ are linked to form a morpholinyl group optionally substituted with one or two $C_1$-$C_3$ alkyl groups or with two substituents that together form a bridged bicyclic moiety having a 2-carbon atom bridge; and Ar is selected from quinolinyl, isoquinolinyl, tetrahydroquinolinyl, and tetrahydroisoquinolinyl, and is optionally substituted with a hydroxyl, amido, methylamido, dimethylamido, or acetylamino group.

7. The aryl-substituted N-alkyl indole of claim 6, wherein m is 1, $L^1$ is —$CH_2$—, $R^1$ is methyl, $R^4$ and $R^5$ are linked to form an unsubstituted morpholinyl group, and Ar is isoquinolinyl optionally substituted with a hydroxyl, methylamido, or acetylamino group.

8. A pharmaceutical formulation comprising a therapeutically effective amount of the aryl-substituted N-alkyl indole of claim 1 and a pharmaceutically acceptable excipient.

9. The pharmaceutical formulation of claim 8, wherein the therapeutically effective amount is a unit dosage.

10. The pharmaceutical formulation of claim 8, comprising an oral dosage form.

11. The pharmaceutical formulation of claim 10, comprising a gummy.

12. The pharmaceutical formulation of claim 8, comprising a suppository.

13. A method for treating a subject affected by a condition responsive to administration of an aryl-substituted N-alkyl indole, comprising administering to the subject, optionally within the context of an ongoing dosage regimen, an effective amount of the compound of claim 1, wherein the condition comprises pain, endometriosis, primary dysmenorrhea, secondary premenstrual syndrome, uterine fibroid pain, menopausal symptoms, adenomyosis, polycystic ovary syndrome, alcoholism, anxiety, autism spectrum disorder, inflammatory bowel disease, celiac disease, systemic lupus erythematosus, Addison's disease, celiac disease, Graves' disease, Hashimoto thyroiditis, myasthenia gravis, psoriasis, Sjogren's disease, pernicious anemia, vasculitis, autoimmune hepatitis, and type 1 diabetes, burns, cardiac disorders, peripheral artery disease, cognitive pain, mild cognitive impairment, non-neurodegenerative dementia, multiple sclerosis, chronic inflammatory demyelinating polyneuropathy (CIDP), Guillain-Barre Syndrome, gingivitis, periodontitis, type 2 diabetes, glucose regulation, drug withdrawal, fibroses, acne, contact dermatitis, eczema, infectious skin ulcers, cellulitis, immunodeficiency, inflammation, ischemia, infertility, fatty liver disease, cirrhosis, hepatitis, Metabolic Syndrome and any condition associated therewith, headaches, nausea, neurological disorders, neurodegenerative disorders, obesity, overweight, conditions caused by or associated with excess weight or obesity, osteoporosis, osteopenia, pelvic pain, attention deficit hyperactivity disorder (ADHD), bipolar disorder, depression, obsessive compulsive disorder (OCD), post-traumatic stress disorder (PTSD), psychosis, schizophrenia, respiratory disorders, seizure disorders, sleep apnea, insomnia, restless leg syndrome, REM sleep dysfunction, or stress.

14. The method of claim 13, wherein the condition comprises pain, inflammation, or both pain and inflammation.

15. The method of claim 14, wherein the condition is pain.

16. The method of claim 15, wherein the pain is neuropathic, nociceptive, or both neuropathic and nociceptive.

17. The method of claim 15, wherein the pain is incident to an injury, chemotherapy, surgery, inflammation, or a disease.

18. The method of claim 13, wherein the subject is female and the condition is endometriosis, dysmenorrhea, premenstrual syndrome, uterine fibroid pain, adenomyosis, polycystic ovary syndrome, menopause, or infertility.

19. The method of claim 18, wherein the condition is endometriosis.

20. The method of claim 1, wherein the aryl-substituted N-alkyl indole is administered vaginally.

21. The method of claim 13, further comprising co-administering at least one additional pharmacologically active agent to the subject.

22. The method of claim 21, wherein the at least one additional pharmacologically active agent is administered to treat the condition.

23. A method of opioid sparing in a subject in need of pain management, comprising co-administering to the subject an effective opioid-sparing dose of the aryl-substituted N-alkyl indole of claim 1 and an opioid analgesic.

24. A method for inducing weight loss in a subject, comprising co-administering to the subject the aryl-substituted N-alkyl indole of claim 1 and a glucagon-like peptide 1 receptor agonist (GLP-1 RA).

* * * * *